(12) United States Patent
Mandler et al.

(10) Patent No.: US 8,828,942 B2
(45) Date of Patent: Sep. 9, 2014

(54) MEANS FOR TREATING SYNUCLEINOPATHIES

(75) Inventors: Markus Mandler, Vienna (AT); Harald Weninger, Vienna (AT); Radmila Santic, Vienna (AT); Christian Lahsnig, Tulln (AT)

(73) Assignee: Affiris AG, Vienna (AT)

( * ) Notice: Subject to any disclaimer, the term of this patent is extended or adjusted under 35 U.S.C. 154(b) by 0 days.

(21) Appl. No.: 13/391,552

(22) PCT Filed: Aug. 20, 2010

(86) PCT No.: PCT/AT2010/000303
§ 371 (c)(1),
(2), (4) Date: Feb. 21, 2012

(87) PCT Pub. No.: WO2011/020133
PCT Pub. Date: Feb. 24, 2011

(65) Prior Publication Data
US 2012/0156234 A1    Jun. 21, 2012

(30) Foreign Application Priority Data

Aug. 21, 2009  (AT) ................. A 1324/2009

(51) Int. Cl.
*A61K 38/08* (2006.01)
*C07K 7/06* (2006.01)

(52) U.S. Cl.
USPC .............. 514/17.7; 424/185.1; 530/328

(58) Field of Classification Search
None
See application file for complete search history.

(56) References Cited

U.S. PATENT DOCUMENTS

| | | |
|---|---|---|
| 2008/0014194 A1 | 1/2008 | Schenk et al. |
| 2008/0175838 A1 | 7/2008 | Schenk et al. |

FOREIGN PATENT DOCUMENTS

| | | |
|---|---|---|
| CN | 101052417 | 10/2007 |
| WO | 2004 041067 | 5/2004 |
| WO | 2006 045037 | 4/2006 |

OTHER PUBLICATIONS

Hong et al. The cDNA cloning and ontogeny of mouse alpha-synuclein, 1998, NeuroReport 9:1239-1243.*

Benner, E.J. et al., "Nitrated Alpha-Synuclein Immunity Accelerates Degeneration of Nigral Dopaminergic Neurons", PLoS One, Issue 1, e1376, pp. 1-20, XP-002606274. (Jan. 2008).

Liang, T. et al.,"Regulation of alpha-synuclein expression in alcohol-preferring and-non preferring rats.", J. Neurochem, vol. 99(2), pp. 470-482, PMID: 17029600. (Oct. 2006) (Abstract only).

Hamilton, B.A., "alpha-Synuclein A53T substitution associated with Parkinson disease also marks the divergence of Old World and New World primates.", Genomics, vol. 83(4), pp. 739-742, PMID 15028296. (Apr. 2004) (Abstract only).

Hashimoto, M. et al., "Beta-synuclein regulates Akt activity in neuronal cells. A possible mechanism for neuroprotection in Parkinson's disease.", J Biol Chem, vol. 279(22), pp. 23622-23629. (May 28, 2004. Epub Mar. 16, 2004) (Abstract only).

Hashimoto, M. et al., "beta-Synuclein inhibits alpha-synuclein aggregation: a possible role as an anti-parkinsonian factor.", Neuron, vol. 32(2), pp. 213-223, PMID 11683992. (Oct. 25, 2001) (Abstract only).

Willats, W.G.T., "Phage display: practicalities and prospects", Plant Molecular Biology, vol. 50, pp. 837-854. (2002).

Burgstaller, P. et al., "Aptamers and aptazymes: Accelerating small molecule drug discovery", Current Opinion in Drug Discovery & Development, vol. 5(5), pp. 690-700, Pharma Press Ltd., ISSN 1367-6733. (2002).

Iwatsubo, T., "Pathological biochemistry of alpha-synucleopathy.", Neuropathology, vols. 27(5), pp. 474-478, PMID: 18018483. (Oct. 2007) (Abstract only).

Famulok M. et al., "Nucleic Acid Aptamers—From Selection in Vitro to Applications in Vivo", Accounts of Chemical Research, vol. 33, No. 9, pp. 591-599. (2000).

Mayer, G. et al., "Controlling small guanine-nucleotide-exchange factor function through cytoplasmic RNA intramers". PNAS, vol. 98, No. 9, pp. 4961-4965, www.pnas.org/cgi/goi/10.107/pnas.091100698. (Apr. 24, 2001).

Singh, M. et al. "Advances in vaccine adjuvants", Nature Biotechnology, vol. 17, pp. 1075-1081, http://biotech.nature.com. (Nov. 1999).

O'Hagan, D.T. et al., "Recent Advances in the Discovery and Delivery of Vaccine Adjuvants", Nature Reviews/Drug Discovery, vol. 2, pp. 727-735. doi:10/1038/mrd1176. (Sep. 2003).

International Search Report issued on Nov. 29, 2010 in PCT/AT10/000303 filed on Aug. 20, 2010.

Office Action as recieved in the corresponding Chinese Patent Application No. 201080047744.9 dated Apr. 2, 2014.

* cited by examiner

*Primary Examiner* — John Ulm
(74) *Attorney, Agent, or Firm* — Oblon, Spivak, McClelland, Maier & Neustadt, L.L.P.

(57) ABSTRACT

The present invention relates to peptides or polypeptides for producing medicaments for preventing and/or treating synucleinopathies.

11 Claims, 5 Drawing Sheets

Alpha-synuclein protein sequence:

```
         10         20         30         40         50         60
MDVFMKGLSK AKEGVVAAAE KTKQGVAEAA GKTKEGVLYV GSKTKEGVVH GVATVAEKTK 70         80         90        100        110        120
EQVTNVGGAV VTGVTAVAQK TVEGAGSIAA ATGFVKKDQL GKNEEGAPQE GILEDMPVDP 130        140
DNEAYEMPSE EGYQDYEPEA
```

MEANS FOR TREATING SYNUCLEINOPATHIES

CROSS-REFERENCE TO RELATED APPLICATIONS

This application is a National Stage of PCT/AT10/000303 filed Aug. 20, 2010 and claims the benefit of Austrian application A 1324/2009 filed Aug. 21,2009.

FIELD OF THE INVENTION

The present invention relates to a medicament to be used to prevent and/or treat synucleinopathies.

BACKGROUND OF THE INVENTION

Synucleinopathies are a diverse group of neurodegenerative disorders that share a common pathologic characteristic: in neuropathologic examinations characteristic lesions can be detected containing abnormal aggregates of alpha-synuclein (alpha-syn, a-syn) protein in selected populations of neurons and glia cells.

Alpha-syn (initially identified as PARK1 and PARK4) is a 140 amino acid protein widely expressed in the neocortex, hippocampus, dentate gyrus, olfactory bulb, striatum, thalamus and cerebellum. Alpha-Syn is also highly expressed in hematopoietic cells including B—, T—, and NK cells as well as monocytes and platelets. The exact role in these cells is not known but it has been implicated in the differentiation of megakaryocytes (platelet precursors).

The most common synucleinopathies include but are not limited to Lewy body disorders (LBDs) like Parkinson's disease (PD), Parkinson's disease with dementia (PDD) and dementia with Lewy bodies (DLB), as well as Multiple System Atrophy (MSA) or Neurodegeneration with Brain Iron Accumulation type I (NBIA Type I). The current treatment options for these diseases include symptomatic medications such as L-dopa, anticholinergic drugs as well as inhibitors of monoamine oxidase. However, all treatment opportunities currently present only lead to symptomatic alleviation but do not induce a long lasting, disease modifying effect in patients.

Lewy body disorders (LBD) are progressive neurodegenerative disorders characterized by tremor, rigidity, bradykinesia and by loss of dopaminergic neurons in the brain. In the case of DLB and PDD signs also include cognitive impairment. Up to 2% of the population above 60 years of age in western countries develop the typical signs of PD/LBD. Currently only symptomatic treatment is available. Unfortunately, these therapies only provide temporary relief from early symptoms and do not halt disease progression. The pathogenesis of PD/LBD is still incompletely understood, but it appears that genetic susceptibility and environmental factors are involved in the development of the disease. Despite all genetic advances, PD/LBD is primarily a sporadic disorder with no known cause (also called idiopathic PD/LBD).

Patients suffering from this disease develop characteristic ubiquitinated intracellular inclusions called Lewy bodies (LBs) in the cortical and subcortical areas of the brain. Especially regions with high content of dopaminergic neurons or neuronal projections show this typical pathologic feature. Recently, several studies could show that the synaptic protein alpha-syn plays a central role in LBD pathogenesis. In LBD, alpha-syn accumulates in LBs throughout affected brain areas. Additionally, it could be demonstrated that single point mutations as well as duplications or multiplications in the alpha-syn gene are associated with rare familial forms of parkinsonism. Importantly, based on results from overexpression studies in transgenic (tg) mice as well as in *Drosophila melanogaster* its key role in the pathogenesis of PD/LBD is underscored as these animal models mimic several characteristics of PD.

Another very important synucleinopathy is Multiple System Atrophy (MSA). MSA is a sporadic neurodegenerative disorder that is characterised by symptoms of L-DOPA-resistant parkinsonism, cerebellar ataxia, and dysautonomia. Patients suffer from multi-system neuronal loss affecting various brain areas including striatum, substantia nigra, cerebellum, pons, as well as the inferior olives and the spinal cord. MSA is characterized by al-pha syn-positive glial cytoplasmic (GCI) and rare neuronal inclusions throughout the central nervous system. These inclusions are associated with striatonigral degeneration, olivopontocerebellar atrophy, and involvement of autonomic nuclei in medulla and spinal cord. The importance of GCIs for the pathogenesis of MSA is generally acknowledged and underscored by recent analysis of transgenic mouse models analysing the effect of alpha-syn overexpression in oligodendroglia. In tg mice overexpressing human alpha-syn both GCI-like aggregates and biochemical markers of MSA were observed.

Although the exact mechanisms by which accumulation of al-pha-syn leads to the typical features of neurodegeneration in synucleopathies are not fully understood, recent studies imply that abnormal formation and accumulation of alpha-syn is involved in the degenerative processes underlying synucleinopathy. Recently, different forms of alpha-syn have been identified in LBs. Beside the full length form of the protein, different forms of modified alpha-syn have been identified including phosphorylated, nitrated, and mono-, di-, or tri-ubiquitinated alpha-syn. In addition, C-terminally truncated forms of the protein, like alpha-syn 1-119, alpha-syn 1-122 and alpha-syn 1-123, have been detected in brain tissue from both transgenic mice and PD cases. It is currently believed that up to 15% of the alpha-syn detected in LBs and lewy neurites is truncated. Previous in vitro studies using truncated alpha-syn could demonstrate that alpha-syn lacking the C-terminal 20-30 amino acids was showing an increased tendency to aggregate and to form filaments found in Lewy-neurites and LBs. These truncated versions could thus act in a similar way as truncated and modified forms of amyloid beta (Aβ) in Alzheimer's disease (AD). These truncated and modified forms of Aβ are thought to act as seed molecules for plaque deposition and show a higher aggregation propensity as well as high neurotoxicity and synaptotoxicity in vivo and in vitro.

Thus full length alpha-syn as well as truncated and/or modified forms of alpha-syn, which are showing potential seeding effects, are then believed to accumulate leading to oligomer-formation. Based on recent studies it is believed that such oligomer-formation for example in the synaptic terminals and axons plays an important role for PD/LBD development and could thus be enhanced by the presence of truncated forms of alpha-syn. Hence, reduction of alpha-syn deposition and oligomerisation should be beneficial in the treatment of synucleopathies, especially of idiopathic LBD/PD and MSA and could present the first strategy for treatment of these neurodegenerative diseases in addition to the mere alleviation of symptoms resulting from current treatment strategies like L-DOPA application.

In Iwatsubo T. (Neuropathology 27 (5) (2007): 474-478) the correlation of alpha-synuclein depositions as well as its phosphorylation with a pathogenesis of alpha-synucleopathies is examined. The author of this publication found that serine 129 of alpha-synuclein deposited in synucleopathy lesions is extensively phosphorylated. US 2007/213253 relates to mutant human alpha-synuclein as well as peptides derived therefrom which may be used for inhibiting the aggregation of the wild-type human alpha-synuclein. In the WO 2004/041067 means and methods for preventing or treating diseases associated with alpha-synuclein aggregation are disclosed which comprise the use of alpha-synuclein fragments. In the US 2003/166558 peptides are described which can be used to induce immune response to protein deposits. US 2005/198694 relates to alpha-synuclein fragments comprising at least 100 amino acids and having a C-terminal deletion of 1 to 23 amino acids.

Liang et al. (J. Neurochem. 99 (2006): 470-482) studied the regulation of alpha-synuclein in rats. They observed that in alcohol preferring rats the expression rate of alpha-synuclein is increased compared to alcohol-non preferring rats.

In Hamilton B A (Genomics 83 (2004): 739-742) the distribution of alpha-synuclein 53Thr and 53Ala in primates is examined.

In US 2005/0037013 immunogenic alpha-synuclein fragments are disclosed which are able to induce an immune response against a specific epitope within residues 70-140 of alpha-synuclein.

WO 2006/045037 relates to C-terminal truncated alpha-synuclein molecules which can be used to screen for agents which have a pharmacological activity useful for treating a Lewy Body Disease.

Although experimental therapies utilizing neurotrophic factors and grafting of dopaminergic cells have yielded promising results, alternative approaches designed to reduce the neuronal accumulation of alpha-syn are required. There is compelling evidence accumulating that alpha-syn aggregates might be targeted by immunotherapy. Indeed, recently a potential for the treatment of synucleopathies has been shown. Tg mice overexpressing human alpha-syn were vaccinated with human alpha-syn protein. In mice that produced high relative affinity antibodies upon vaccination, there was decreased accumulation of aggregated alpha-syn in neuronal cell bodies and synapses which was associated with reduced neurodegeneration. Furthermore, antibodies produced by immunized animals also detected abnormal aggregated forms of alpha-syn associated with the neuronal membrane and promoted the degradation of these aggregates, probably via lysosomal pathways. Similar effects were observed using passive immunotherapy with an exogenously applied alpha-syn-specific antibody. These results suggest that vaccination is effective in reducing neuronal accumulation of alpha-syn aggregates and that further development of this approach might elicit beneficial effects in the treatment of LBD and synucleinopathies.

BRIEF SUMMARY OF THE INVENTION

It is an object of the present invention to provide a medicament to prevent and treat synucleinopathies on the basis of a vaccine.

BRIEF DESCRIPTION OF THE DRAWINGS

The present invention is further illustrated in the following figures and examples, however, without being restricted thereto.

FIG. 1 shows the sequence of full length alpha-synuclein (140aa; swiss prot entry: P37840) and the sequence used to create a monoclonal antibody for detection of full length alpha-synuclein as well as C-terminally truncated and modified versions thereof. The peptide at position 100-109 used for generation of the monoclonal antibody is underlined. The peptide (p4453) was coupled to a C at C-terminal position.

The peptides p4446 (alpha-synuclein), p4453 (human epitope used to create the antibody tested) are detected by the antibody. The original epitope p4453 was N- or C-terminally truncated and used for ELISA to define the minimal epitope required for specific binding. The peptides p5399 and p5403 lost binding to the monoclonal antibody 12-9-9. Thus the minimal sequence needed for binding of 12-9-9 is predicted as KNEEGAP located at position 102-108 of alpha-synuclein, while truncation of one of the flanking amino acids abolished the binding. Data are presented in a linear scale.

Figure 4:
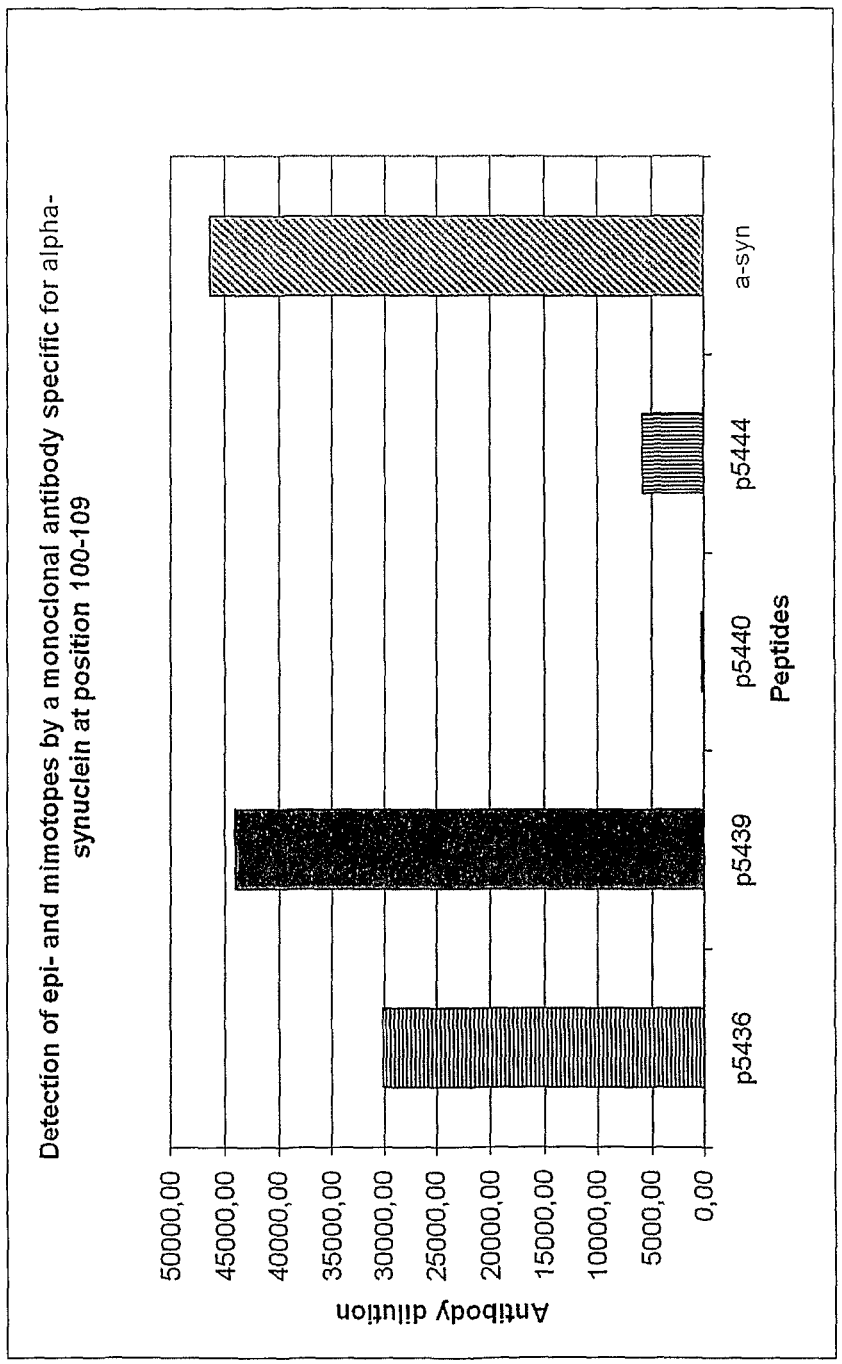

FIG. 4 shows detection of epitopes and mimotopes by ELISA using a monoclonal specific for human alpha-synuclein at position 100-109. Alpha-Synuclein as well as the peptides p5436 (human minimal epitope) and the mimotopes p5439 are detected similarly by the monoclonal antibody 12-9-9. The mimotope p5440 is not detected, while mimotope p5444 is detected much weaker than the human epitope by the monoclonal antibody 12-9-9.

Figure 5:
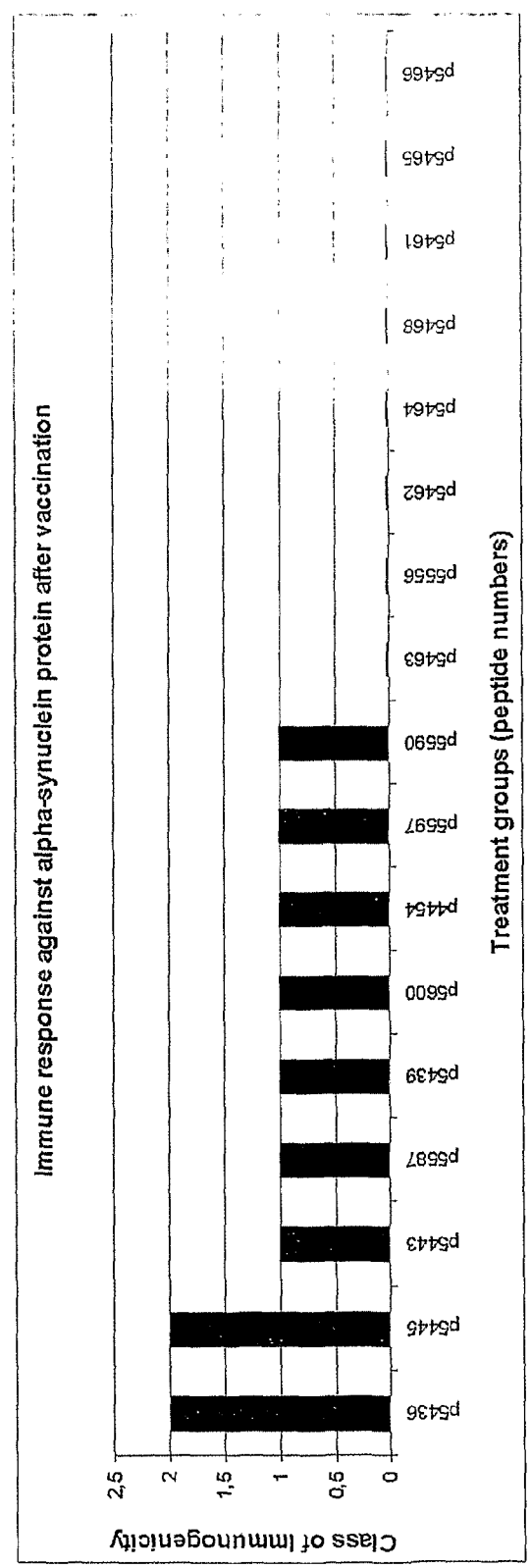

FIG. 5 shows the induction of immune response against alpha-synuclein after peptide immunization. Sera of immunized mice (p5436 to p5590) show titers against alpha-synuclein after 3 vaccinations. Sera of immunized mice (p5463 to p5466) do not detect alpha synuclein (Titers measured in ELISA are around or below 1:50 half-max). Class of immunogenicity was defined as follows: Class 2: peptides inducing an immune response with OD halfmax higher than 1:1000. Class 1: peptides inducing an immune response with OD halfmax between 1000 and 51. Class 0: peptides inducing no or an very low immune resonse with OD halfmax around 50 or lower.

DETAILED DESCRIPTION OF THE INVENTION

The present invention relates to the provision of at least one peptide or polypeptide comprising the amino acid sequence $(X_1)_n X_2 X_3 X_4 X_5 G X_6 P (X_7)_m$ (SEQ ID NO: 78)    (Formula I), wherein
$X_1$ is any amino acid residue,
$X_2$ is an amino acid residue selected from the group consisting of lysine (K), arginine (R), alanine (A) and histidine (H),
$X_3$ is an amino acid residue selected from the group consisting of asparagine (N), glutamine (Q), serine (S), glycine (G) and alanine (A), preferably asparagine (N), serine (S), glycine (G) and alanine (A),
$X_4$ is an amino acid residue selected from the group consisting of glutamic acid (E), aspartic acid (D) and alanine (A),
$X_5$ is an amino acid residue selected from the group consisting of glutamic acid (E) and aspartic acid (D),
$X_6$ is an amino acid residue selected from the group consisting of alanine (A) and tyrosine (Y),
$X_7$ is any amino acid residue,
n and m, independently, are 0 or an integer of more than 0, and wherein the amino acid sequence according to Formula I is not identical with, or does not comprise the 7-mer polypeptide fragment of alpha-synuclein having the amino acid sequence KNEEGAP (SEQ ID NO: 139), said at least one peptide or polypeptide having a binding capacity to an antibody which is specific for an epitope of alpha-synuclein comprising the amino acid sequence KNEEGAP (SEQ ID NO: 139), for use in preventing and/or treating synucleinopathies.

These peptides or polypeptides according to the present invention can be provided in compositions suitable for the intended use for preventing and/or treating synucleinopathies, especially in pharmaceutical compositions, preferably combined with a pharmaceutically acceptable carrier. Such pharmaceutical compositions can be administered to a patient in need thereof in an effective amount to achieve the preventive and/or therapeutic effect.

The peptides and polypeptide according to the present invention are able to induce the in vivo formation of antibodies directed (binding) to alpha-synuclein and fragments thereof, in particular to fragments of alpha-synuclein comprising the amino acid sequence KNEEGAP (SEQ ID NO: 139). Antibodies directed (binding) to said peptides and polypeptides, however, show no or substantially no immune reactivity to beta-synuclein (beta-syn, b-syn). Therefore, unlike the original alpha-synuclein or fragment(s) thereof, the peptides and polypeptides according to the present invention provide a specificity towards the disease related agent and avoid cross reactivity with disease unrelated synucleins. This strongly suggests significant superiority regarding efficacy and safety, the latter in particular because of the neuroprotective characteristics that have been described for beta-synuclein (Hashimoto M. et al., J Biol. Chem. 2004 May 28; 279(22):23622-9. Hashimoto M, Neuron. 2001 Oct. 25; 32(2):213-23).

The alpha-synuclein specific antibodies induced by the administration of the compounds of the present invention might not only bind to monomeric forms of alpha-synuclein but also to multimeric forms. This allows to reduce the amount of oligomers of alpha-synuclein in the body of an individual to be treated. The reduction of alpha-synuclein is particularly beneficial in the treatment of synucleopathies.

The amino acid sequence $(X_1)_n X_2 X_3 X_4 X_5 G X_6 P(X_7)_m$ (SEQ ID NO: 78) is considered to be a mimotope of the epitope of alpha-synuclein comprising the amino acid sequence KNEEGAP (SEQ ID NO: 139). According to the present invention the term "mimotope" refers to a molecule which has a conformation that has a topology equivalent to the epitope of which it is a mimic. The mimotope binds to the same antigen-binding region of an antibody which binds immunospecifically to a desired antigen. The mimotope will elicit an immunological response in a host that is reactive to the antigen to which it is a mimic. The mimotope may also act as a competitor for the epitope of which it is a mimic in in vitro inhibition assays (e.g. ELISA inhibition assays) which involve the epitope and an antibody binding to said epitope. However, a mimotope of the present invention may not necessarily prevent or compete with the binding of the epitope of which it is a mimic in an in vitro inhibition assay although it is capable to induce a specific immune response when administered to a mammal.

As used herein, the term "epitope" refers to an immunogenic region of an antigen which is recognized by a particular anti-body molecule. In general, an antigen will possess one or more epitopes, each capable of binding an antibody that recognizes the particular epitope.

The mimotopes of the present invention can be synthetically produced by chemical synthesis methods which are well known in the art, either as an isolated peptide or as a part of another peptide or polypeptide. Alternatively, the peptide mimotope can be produced in a microorganism which produces the peptide mimotope which is then isolated and if desired, further purified. The peptide mimotope can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the peptide mimotope include *E. coli*, *B. subtilis* or any other bacterium that is capable of expressing peptides such as the peptide mimotope. Suitable yeast types for expressing the peptide mimotope include *Saccharomyces* cerevisiae, *Schizosaccharomyces pombe*, *Candida*, *Pichia pastoris* or any other yeast capable of expressing peptides. Corresponding methods are well known in the art. Also methods for isolating and purifying recombinantly produced peptides are well known in the art and include e.g. gel filtration, affinity chromatography, ion exchange chromatography etc.

To facilitate isolation of the peptide mimotope, a fusion polypeptide may be made wherein the peptide mimotope is translationally fused (covalently linked) to a heterologous polypeptide which enables isolation by affinity chromatography. Typical heterologous polypeptides are His-Tag (e.g. His$_6$; 6 histidine residues) (SEQ ID NO: 140)), GST-Tag (Glutathione-S-transferase) etc. The fusion polypeptide facilitates not only the purification of the mimotopes but can also prevent the mimotope polypeptide from being degraded during purification. If it is desired to remove the heterologous polypeptide after purification the fusion polypeptide may comprise a cleavage site at the junction between the peptide mimotope and the heterologous polypeptide. The cleavage site consists of an amino acid sequence that is cleaved with an enzyme specific for the amino acid sequence at the site (e.g. proteases).

According to a preferred embodiment of the present invention, $X_2$ is an amino acid residue selected from the group consisting of lysine (K) and arginine (R) and/or $X_6$ is alanine (A).

According to a particularly preferred embodiment of the present invention, the peptide or polypeptide comprises an amino acid sequence selected from the group consisting of $(X_1)_n$KNDEGAP$(X_7)_m$ (SEQ ID NO: 87), $(X_1)_n$ANEEGAP$(X_7)_m$ (SEQ ID NO: 79), $(X_1)_n$KAEEGAP$(X_7)_m$ (SEQ ID NO: 80), $(X_1)_n$KNAEGAP$(X_7)_m$ (SEQ ID NO: 81), $(X_1)_n$RNEEGAP$(X_7)_m$ (SEQ ID NO: 85), $(X_1)_n$HNEEGAP$(X_7)_m$ (SEQ ID NO: 86), $(X_1)_n$KNEDGAP$(X_7)_m$ (SEQ ID NO: 88), $(X_1)_n$KQEEGAP$(X_7)_m$ (SEQ ID NO: 89), $(X_1)_n$KSEEGAP$(X_7)_m$ (SEQ ID NO: 90), $(X_1)_n$KNDDGAP$(X_7)_m$ (SEQ ID NO: 91), $(X_1)_n$RNDEGAP$(X_7)_m$ (SEQ ID NO: 115), $(X_1)_n$RNEDGAP$(X_7)_m$ (SEQ ID NO: 116), $(X_1)_n$RQEEGAP$(X_7)_m$ (SEQ ID NO: 117), $(X_1)_n$RSEEGAP$(X_7)_m$ (SEQ ID NO: 118), $(X_1)_n$ANDEGAP$(X_7)_m$ (SEQ ID NO: 119), $(X_1)_n$ANEDGAP$(X_7)_m$ (SEQ ID NO: 120), $(X_1)_n$HSEEGAP$(X_7)_m$ (SEQ ID NO: 121), $(X_1)_n$ASEEGAP$(X_7)_m$ (SEQ ID NO: 122), $(X_1)_n$HNEDGAP$(X_7)_m$ (SEQ ID NO: 123), $(X_1)_n$HNDEGAP$(X_7)_m$ (SEQ ID NO: 124), $(X_1)_n$RNAEGAP$(X_7)_m$ (SEQ ID NO: 125), $(X_1)_n$HNAEGAP$(X_7)_m$ (SEQ ID NO: 126), $(X_1)_n$KSAEGAP$(X_7)_m$ (SEQ ID NO: 127), $(X_1)_n$KSDEGAP$(X_7)_m$ (SEQ ID NO: 128), $(X_1)_n$KSEDGAP$(X_7)_m$ (SEQ ID NO: 129), $(X_1)_n$RQDEGAP$(X_7)_m$ (SEQ ID NO: 141), $(X_1)_n$RQEDGAP$(X_7)_m$ (SEQ ID NO: 131), $(X_1)_n$HSAEGAP$(X_7)_m$ (SEQ ID NO: 132), $(X_1)_n$RSAEGAP$(X_7)_m$ (SEQ ID NO: 133), $(X_1)_n$RSDEGAP$(X_7)_m$ (SEQ ID NO: 134), $(X_1)_n$RSEDGAP$(X_7)_m$ (SEQ ID NO: 135), $(X_1)_n$HSDEGAP$(X_7)_m$ (SEQ ID NO: 136), $(X_1)_n$HSEDGAP$(X_7)_m$ (SEQ ID NO: 137), $(X_1)_n$RQDDGAP$(X_7)_m$ (SEQ ID NO: 138), preferably $(X_1)_n$KNDEGAP$(X_2)_m$ (SEQ ID NO: 87), $(X_1)_n$RNEEGAP$(X_2)_m$ (SEQ ID NO: 85), $(X_1)_n$RNDEGAP$(X_2)_m$ (SEQ ID NO: 115), $(X_1)_n$KNAEGAP$(X_2)_m$ (SEQ ID NO: 81), $(X_1)_n$KSDEGAP$(X_2)_m$ (SEQ ID NO: 128), $(X_1)_n$RNAEGAP$(X_2)_m$ (SEQ ID NO: 125)or $(X_1)_n$RSEEGAP$(X_2)_m$ (SEQ ID NO: 118).

It turned out that not only peptides and polypeptides according to formula I can be used in the treatment and prevention of synucleinopathies, but also other peptides and polypeptides. Therefore, another aspect of the present invention relates to at least one peptide or polypeptide comprising an amino acid sequence selected from the group consisting of $(X_1)_n$KNEAGAP$(X_7)_m$ (SEQ ID NO: 82), $(X_1)_n$KNEEAAP$(X_7)_m$ (SEQ ID NO: 83), $(X_1)_n$KNEEGAA$(X_7)_m$ (SEQ ID NO: 84), $(X_1)_n$KPSFKNE$(X_7)_m$ (SEQ ID NO: 92), $(X_1)_n$QPSFAME$(X_7)_m$ (SEQ ID NO: 93), $(X_1)_n$SPSFKQE$(X_7)_m$ (SEQ ID NO: 94), $(X_1)_n$TPSWKGE$(X_7)_m$ (SEQ ID NO: 95), $(X_1)_n$DPSFALE$(X_7)_m$ (SEQ ID NO: 96), $(X_1)_n$LPSFRLE$(X_7)_m$ (SEQ ID NO: 97), $(X_1)_n$EPNSRMD$(X_7)_m$ (SEQ ID NO: 98), $(X_1)_n$QPSSKLD$(X_7)_m$ (SEQ ID NO: 99), $(X_1)_n$HIHQSKFFDAPP$(X_7)_m$ (SEQ ID NO: 100), $(X_1)_n$QASFAME$(X_7)_m$ (SEQ ID NO: 101), $(X_1)_n$TASWKGE$(X_7)_m$ (SEQ ID NO: 102), $(X_1)_n$QASSKLD$(X_7)_m$ (SEQ ID NO: 103), $(X_1)_n$QPAFAME$(X_7)_m$ (SEQ ID NO: 104), $(X_1)_n$TPAWKGE$(X_7)_m$ (SEQ ID NO: 105), $(X_1)_n$QPASKLD$(X_7)_m$ (SEQ ID NO: 106), $(X_1)_n$QPSFAMA$(X_7)_m$ (SEQ ID NO: 107), $(X_1)_n$TPSWKGA$(X_7)_m$ (SEQ ID NO: 108), $(X_1)_n$QPSSKLA$(X_7)_m$ (SEQ ID NO: 109), $(X_1)_n$APSWKGE$(X_7)_m$ (SEQ ID NO: 110), $(X_1)_n$TPSAKGE$(X_7)_m$ (SEQ ID NO: 111), $(X_1)_n$TPSWAGE$(X_7)_m$ (SEQ ID NO: 112), $(X_1)_n$TPSWKAE$(X_7)_m$ (SEQ ID NO: 113), $(X_1)_n$TPSWKGE$(X_7)_m$ (SEQ ID NO: 114), especially an amino acid sequence selected from the group consisting of $(X_1)_n$QASFAME$(X_7)_m$ (SEQ ID NO: 101), $(X_1)_n$TASWKGE$(X_7)_m$ (SEQ ID NO: 102), $(X_1)_n$QASSKLD$(X_7)_m$ (SEQ ID NO: 103), $(X_1)_n$TPAWKGE$(X_7)_m$ (SEQ ID NO: 105), $(X_1)_n$TPSWAGE$(X_7)_m$ (SEQ ID NO: 112), $(X_1)_n$TPSWKGE$(X_7)_m$ (SEQ ID NO: 95),
wherein
$X_1$ is any amino acid residue,
$X_7$ is any amino acid residue,
n and m, independently, are 0 or an integer of more than 0,
said at least one peptide or polypeptide having a binding capacity to an antibody which is specific for an epitope of alpha-synuclein comprising the amino acid sequence KNEEGAP (SEQ ID NO: 139),
for use in preventing and/or treating synucleinopathies, especially for the production of a medicament therefor.

The peptides and polypeptides of the present invention may also be modified at or nearby their N- and/or C-termini so that at said positions a cysteine residue is bound thereto. In a preferred embodiment terminally positioned (located at the N- and C-termini of the peptide) cysteine residues are used to cross-link said molecules with carrier molecules such as KLH or to cyclize the peptides through a disulfide bond. Therefore, n and/or m are preferably 1 and $X_1$ and/or $X_7$ are preferably cysteine (C).

The mimotopes of the present invention may also be used in various assays and kits, in particular in immunological assays and kits. Therefore, it is particularly preferred that the peptides and polypeptides of the present invention may be part of another peptide or polypeptide, particularly an enzyme which is used as a reporter in immunological assays. Such reporter enzymes include e.g. alkaline phosphatase or horseradish peroxidase.

The alpha-synuclein mimotopes according to the present invention preferably are antigenic polypeptides which in their amino acid sequence vary from the amino acid sequence of alpha-synuclein or of fragments of alpha-synuclein. In this respect, the inventive mimotopes may not only comprise amino acid substitutions of one or more naturally occurring amino acid residues but also of one or more non-natural amino acids (i.e. not from the 20 "classical" amino acids) or they may be completely assembled of such non-natural amino acids. Moreover, the inventive antigens which induce anti-alpha-synuclein antibodies may be assembled of D- or L-amino acids or of combinations of DL-amino acids and, optionally, they may have been changed by further modifications, ring closures or derivatizations. Suitable antialpha-synuclein-antibody-inducing antigens may be provided from commercially available peptide libraries. Preferably, these peptides are at least 7 amino acids, and preferred lengths may be up to 16, preferably up to 14 or 20 amino acids residues (e.g. 7 or 8 to 20, 7 or 8 to 16 etc.). Thus, the peptide or polypeptide of the present invention comprises 7 to 30, preferably 7 to 20, more preferably 7 to 16, most preferably 8, amino acid residues. According to the invention, however, also longer peptides may very well be employed as anti-alpha-synuclein-antibody-inducing antigens. Furthermore the mimotopes of the present invention may also be part of a polypeptide and consequently comprising at their N- and/or C-terminus at least one further amino acid residue.

For preparing alpha-synuclein mimotopes (i.e. anti-alpha-synuclein-antibody-inducing antigens), of course also phage libraries, peptide libraries are suitable, for instance produced by means of combinatorial chemistry or obtained by means of high throughput screening techniques for the most varying structures (Display: A Laboratory Manual by Carlos F. Barbas (Editor), et al.; Willats W G Phage display: practicalities and prospects. Plant Mol. Biol. 2002 December; 50(6):837-54).

Furthermore, according to the invention also anti-alpha-synuclein-antibody-inducing antigens based on nucleic acids ("aptamers") may be employed, and these, too, may be found with the most varying (oligonucleotide) libraries (e.g. with 2-180 nucleic acid residues) (e.g. Burgstaller et al., Curr. Opin. Drug Discov. Dev. 5(5) (2002), 690-700; Famulok et al., Acc. Chem. Res. 33 (2000), 591-599; Mayer et al., PNAS 98 (2001), 4961-4965, etc.). In anti-alpha-synuclein-antibody-inducing antigens based on nucleic acids, the nucleic acid backbone can be provided e.g. by the natural phosphordiester compounds, or also by phosphorotioates or combinations or chemical variations (e.g. as PNA), wherein as bases, according to the invention primarily U, T, A, C, G, H and mC can be employed. The 2'-residues of the nucleotides which can be used according to the present invention preferably are H, OH, F, Cl, NH$_2$, O-methyl, O-ethyl, O-propyl or O-butyl, wherein the nucleic acids may also be differently modified, i.e. for instance with protective groups, as they are commonly employed in oligonucleotide synthesis. Thus, aptamer-based anti-alpha-synuclein-antibody-inducing antigens are also preferred anti-alpha-synuclein-antibody-inducing antigens within the scope of the present invention.

According to the present invention the term "synucleinopathy" includes all neurodegenerative disorders characterized by pathological synuclein aggregations. Several neurodegenerative disorders including Parkinson's Disease (PD), Lewy Body Disease (LBD), Diffuse Lewy Body Disease (DLBD), Dementia with Lewy Bodies (DLB), Parkinsonism with Dementia (PDD), Multiple System Atrophy (MSA) and Neurodegeneration with Brain Iron Accumulation type I (NBIA Type I) are collectively grouped as synucleinopathies.

The peptides and polypeptides according to the present invention may be employed not only for treating synucleinopathies but also to prevent said diseases in individuals being at risk of developing a synucleinopathy (e.g. predisposed, for example genetically predisposed, to developing a synucleinopathy).

The abbreviations for the amino acid residues disclosed in the present invention follow the IUPAC recommendations:

| Amino Acid | 3-Letter Code | 1-Letter Code |
|---|---|---|
| Alanine | Ala | A |
| Arginine | Arg | R |
| Asparagine | Asn | N |
| Aspartic | Asp | D |
| Cysteine | Cys | C |
| Glutamic | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The peptides and polypeptides of the present invention may also be part of a polypeptide comprising 7 to 30 amino acid residues. Consequently n and m may independently be an integer selected from the group of 1, 2, 3, 4, 5, 6, 7, 8, 9, 10, 11, 12, 13, 14, 15, 20 and 25.

The at least one peptide or polypeptide according to the present invention may consist of the amino acid sequence $(X_1)_n X_2 X_3 X_4 X_5 G X_6 P(X_7)_m$ (SEQ ID NO: 142), wherein n and m are independently 0 or 1 or being part of a polypeptide which comprises at least 7 amino acid residues, preferably at least 10 amino acid residues, more preferably at least 15 amino acid residue, and/or a maximum of 50 amino acid residues, preferably a maximum of 30 amino acid residues, more preferably of 16 amino acid residues.

Surprisingly, it turned out that the compounds according to the present invention comprising or consisting of the amino acid sequences listed above are particularly suited to be used for the manufacture of a medicament to be used to treat or prevent synucleinopathies. These peptides (mimotopes) are able to induce the in vivo formation of antibodies directed to the original epitope of human alpha-synuclein comprising the amino acid sequence KNEEGAP (SEQ ID NO: 139) and human alpha-synuclein protein itself. Said peptides (mimotopes) are, however, not able to induce immune reactivity against human beta-synuclein protein. The peptide induced antibodies are responsible for the removal of alpha-synuclein (which is involved in the formation of alpha-synuclein aggregates, Lewy bodies) and/or for the dissolution of alpha-synuclein aggregates (Lewy bodies) in an individual.

The peptides and polypeptides according to the present invention may be used for the preparation of a medicament, in particular a vaccine, which can be used to treat alpha-synucleinopathy, whereby the medicament is particularly suited to treat synucleinopathy selected from the group consisting of Parkinson's Disease (PD), Lewy Body Disease (LBD), Diffuse Lewy Body Disease (DLBD), Dementia with Lewy Bodies (DLB), Parkinsonism with Dementia (PDD), Multiple System Atrophy (MSA) and Neurodegeneration with Brain Iron Accumulation type I (NBIA Type I).

According to a preferred embodiment of the present invention the at least one peptide or polypeptide is coupled to a pharmaceutically acceptable carrier, preferably KLH (Keyhole Limpet Hemocyanin), tetanus toxoid, albumin-binding protein, bovine serum albumin, a dendrimer (MAP; Biol. Chem. 358: 581), peptide linkers (or flanking regions) as well as the adjuvant substances described in Singh at al., Nat. Biotech. 17 (1999), 1075-1081 (in particular those in Table 1 of that document), and O'Hagan at al., Nature Reviews, Drug Discovery 2 (9) (2003), 727-735 (in particular the endogenous immuno-potentiating compounds and delivery systems described therein), and others or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminium composition, in particular aluminium hydroxide. Of course, also adjuvants like MF59 aluminium phosphate, calcium phosphate, cytokines (e.g., IL-2, IL-12, GM-CSF), saponins (e.g., QS21), MDP derivatives, CpG oligos, IC31, LPS, MPL, polyphosphazenes, emulsions (e.g., Freund's, SAF), liposomes, virosomes, iscoms, cochleates, PLG microparticles, poloxamer particles, virus-like particles, heat-labile enterotoxin (LT), cholera toxin (CT), mutant toxins (e.g., LTK63 and LTR72), microparticles and/or polymerized liposomes may be used.

The peptide or polypeptide of the present invention is preferably bound to the carrier or adjuvant via a linker, which is selected from the group consisting of NHS-poly (ethylene oxide) (PEO) (e.g. NHS-$PEO_4$-maleimide).

A vaccine which comprises the present compound (mimotope) and the pharmaceutically acceptable carrier may be administered by any suitable mode of application, e.g. i.d., i.p., i.m., intranasally, orally, subcutaneously, etc. and in any suitable delivery device (O'Hagan at al., Nature Reviews, Drug Discovery 2 (9), (2003), 727-735). The compound of the present invention is preferably formulated for subcutaneous, intradermal or intramuscular administration (see e.g. "Handbook of Pharmaceutical Manufacturing Formulations", Sarfaraz Niazi, CRC Press Inc, 2004).

Typically, the vaccine contains the compound according to the invention in an amount of from 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. Typically, the vaccine may also contain auxiliary substances, e.g. buffers, stabilizers etc. Preferably, such auxiliary substances, e.g. a pharmaceutically acceptable excipient, such as water, buffer and/or stabilisers, are contained in an amount of 1 to 99% (weight), more preferred 5 to 80% (weight), especially 10 to 70% (weight). Possible administration regimes include a weekly, biweekly, four-weekly (monthly) or bimonthly treatment for about 1 to 12 months; however, also 2 to 5, especially 3 to 4, initial vaccine administrations (in one or two months), followed by boaster vaccinations 6 to 12 months thereafter or even years thereafter are preferred—besides other regimes already suggested for other vaccines. Another aspect of the present invention relates to a peptide having an amino acid sequence selected from the group consisting of $(X_1)_n$KNDEGAP$(X_7)_m$ (SEQ ID NO: 143), $(X_1)_n$ANEEGAP$(X_7)_m$ (SEQ ID NO: 144), $(X_1)_n$KAEEGAP$(X_7)_m$ (SEQ ID NO: 145), $(X_1)_n$KNAEGAP$(X_7)_m$ (SEQ ID NO: 146), $(X_1)_n$KNEAGAP$(X_7)_m$ (SEQ ID NO: 147), $(X_1)_n$KNEEAAP$(X_7)_m$ (SEQ ID NO:

148), $(X_1)_n$KNEEGAA$(X_7)_m$ (SEQ ID NO: 149), $(X_1)_n$RNEEGAP$(X_7)_m$ (SEQ ID NO: 150), $(X_1)_n$HNEEGAP$(X_7)_m$ (SEQ ID NO: 151), $(X_1)_n$KNEDGAP$(X_7)_m$ (SEQ ID NO: 152), $(X_1)_n$KQEEGAP$(X_7)_m$ (SEQ ID NO: 153), $(X_1)_n$KSEEGAP$(X_7)_m$ (SEQ ID NO: 154), $(X_1)_n$KNDDGAP$(X_7)_m$ (SEQ ID NO: 155), $(X_1)_n$KPSFKNE $(X_7)_m$ (SEQ ID NO: 156),$(X_1)_n$QPSFAME$(X_7)_m$ (SEQ ID NO: 157), $(X_1)_n$SPSFKQE$(X_7)_m$ (SEQ ID NO: 158), $(X_1)_n$TPSWKGE$(X_7)_m$ (SEQ ID NO: 159), $(X_1)_n$QPSFALE$(X_7)_m$ (SEQ ID NO: 160), $(X_1)_n$LPSFRLE $(X_7)_m$ (SEQ ID NO: 161), $(X_1)_n$EPNSRMD$(X_7)_m$ (SEQ ID NO: 162),$(X_1)_n$QPSSKLD$(X_7)_m$ (SEQ ID NO: 163), $(X_1)_n$HIHQSKFFDAPP$(X_7)_m$ (SEQ ID NO: 164), $(X_1)_n$QASFAME$(X_7)_m$ (SEQ ID NO: 165), $(X_1)_n$TASWKGE$(X_7)_m$ (SEQ ID NO: 166), $(X_1)_n$QASSKLD $(X_7)_m$ (SEQ ID NO: 167), $(X_1)_n$QPAFAME$(X_7)_m$ (SEQ ID NO: 168), $(X_1)_n$TPAWKGE$(X_7)_m$ (SEQ ID NO: 169), $(X_1)_n$QPASKLD$(X_7)_m$ (SEQ ID NO: 170), $(X_1)_n$QPSFAMA$(X_7)_m$ (SEQ ID NO: 171), $(X_1)_n$TPSWKGA$(X_7)_m$ (SEQ ID NO: 172), $(X_1)_n$QPSSKLA$(X_7)_m$ (SEQ ID NO: 173), $(X_1)_n$APSWKGE$(X_7)_m$ (SEQ ID NO: 174), $(X_1)_n$TPSAKGE$(X_7)_m$ (SEQ ID NO: 175), $(X_1)_n$TPSWAGE$(X_7)_m$ (SEQ ID NO: 176), $(X_1)_n$TPSWKAE$(X_7)_m$ (SEQ ID NO: 177), $(X_1)_n$TPSWKGE$(X_7)_m$ (SEQ ID NO: 178), $(X_1)_n$RNDEGAP$(X_7)_m$ (SEQ ID NO: 179), $(X_1)_n$RNEDGAP$(X_7)_m$ (SEQ ID NO: 180), $(X_1)_n$RQEEGAP$(X_7)_m$ (SEQ ID NO: 181), $(X_1)_n$RSEEGAP$(X_7)_m$ (SEQ ID NO: 182), $(X_1)_n$ANDEGAP$(X_7)_m$ (SEQ ID NO: 183), $(X_1)_n$ANEDGAP$(X_7)_m$ (SEQ ID NO: 184), $(X_1)_n$KSEEGAP$(X_7)_m$ (SEQ ID NO: 185), $(X_1)_n$ASEEGAP$(X_7)_m$ (SEQ ID NO: 186), $(X_1)_n$HNEDGAP$(X_7)_m$ (SEQ ID NO: 187), $(X_1)_n$HNDEGAP$(X_7)_m$ (SEQ ID NO: 188), $(X_1)_n$RNAEGAP$(X_7)_m$ (SEQ ID NO: 189), $(X_1)_n$HNAEGAP$(X_7)_m$ (SEQ ID NO: 190), $(X_1)_n$KSAEGAP$(X_7)_m$ (SEQ ID NO: 191), $(X_1)_n$KSDEGAP$(X_7)_m$ (SEQ ID NO: 192), $(X_1)_n$KSEDGAP$(X_7)_m$ (SEQ ID NO: 193), $(X_1)_n$RQDEGAP$(X_7)_m$ (SEQ ID NO: 194), $(X_1)_n$RQEDGAP $(X_7)_m$ (SEQ ID NO: 195), $(X_1)_n$HSAEGAP$(X_7)_m$ (SEQ ID NO: 196), $(X_1)_n$RSAEGAP$(X_7)_m$ (SEQ ID NO: 197), $(X_1)_n$RSDEGAP$(X_7)_m$ (SEQ ID NO: 198), $(X_1)_n$RSEDGAP$(X_7)_m$ (SEQ ID NO: 199), $(X_1)_n$HSDEGAP$(X_7)_m$ (SEQ ID NO: 200), $(X_1)_n$HSEDGAP$(X_7)_m$ (SEQ ID NO: 201) and $(X_1)_n$RQDDGAP$(X_7)_m$ (SEQ ID NO: 202), especially an amino acid sequence selected from the group consisting of $(X_1)_n$KNDEGAP$(X_7)_m$ (SEQ ID NO: 143), $(X_1)_n$ANEEGAP$(X_7)_m$ (SEQ ID NO: 144), $(X_1)_n$KAEEGAP$(X_7)_m$ (SEQ ID NO: 145), $(X_1)_n$KNAEGAP$(X_7)_m$ (SEQ ID NO: 146), $(X_1)_n$RNEEGAP$(X_7)_m$ (SEQ ID NO: 150), $(X_1)_n$HNEEGAP$(X_7)_m$ (SEQ ID NO: 151), $(X_1)_n$KNEDGAP$(X_7)_m$ (SEQ ID NO: 152), $(X_1)_n$KQEEGAP$(X_7)_m$ (SEQ ID NO: 153), $(X_1)_n$KSEEGAP$(X_7)_m$ (SEQ ID NO: 154), $(X_1)_n$KNDDGAP$(X_7)_m$ (SEQ ID NO: 155), $(X_1)_n$QASFAME$(X_7)_m$ (SEQ ID NO: 165), $(X_1)_n$TASWKGE$(X_7)_m$ (SEQ ID NO: 166), $(X_1)_n$QASSKLD$(X_7)_m$ (SEQ ID NO: 167), $(X_1)_n$TPAWKGE$(X_7)_m$ (SEQ ID NO: 169), $(X_1)_n$TPSWAGE$(X_7)_m$ (SEQ ID NO: 176), $(X_1)_n$TPSWKGE$(X_7)_m$ (SEQ ID NO: 178), $(X_1)_n$RNDEGAP$(X_7)_m$ (SEQ ID NO: 179), $(X_1)_n$RNEDGAP$(X_7)_m$ (SEQ ID NO: 180), $(X_1)_n$RQEEGAP$(X_7)_m$ (SEQ ID NO: 181), $(X_1)_n$RSEEGAP$(X_7)_m$ (SEQ ID NO: 182), $(X_1)_n$ANDEGAP$(X_7)_m$ (SEQ ID NO: 183), $(X_1)_n$ANEDGAP$(X_7)_m$ (SEQ ID NO: 184), $(X_1)_n$HSEEGAP$(X_7)_m$ (SEQ ID NO: 185), $(X_1)_n$ASEEGAP$(X_7)_m$ (SEQ ID NO: 186), $(X_1)_n$HNEDGAP$(X_7)_m$ (SEQ ID NO: 187), $(X_1)_n$HNDEGAP$(X_7)_m$ (SEQ ID NO: 188), $(X_1)_n$RNAEGAP$(X_7)_m$ (SEQ ID NO: 189), $(X_1)_n$HNAEGAP$(X_7)_m$ (SEQ ID NO: 190), $(X_1)_n$KSAEGAP$(X_7)_m$ (SEQ ID NO: 191), $(X_1)_n$KSDEGAP$(X_7)_m$ (SEQ ID NO: 192), $(X_1)_n$KSEDGAP$(X_7)_m$ (SEQ ID NO: 193), $(X_1)_n$RQDEGAP$(X_7)_m$ (SEQ ID NO: 194), $(X_1)_n$RQEDGAP$(X_7)_m$ (SEQ ID NO: 195), $(X_1)_n$HSAEGAP$(X_7)_m$ (SEQ ID NO: 196), $(X_1)_n$RSAEGAP$(X_7)_m$ (SEQ ID NO: 197), $(X_1)_n$RSDEGAP$(X_7)_m$ (SEQ ID NO: 198), $(X_1)_n$RSEDGAP$(X_7)_m$ (SEQ ID NO: 199), $(X_1)_n$HSDEGAP$(X_7)_m$ (SEQ ID NO: 200), $(X_1)_n$HSEDGAP$(X_7)_m$ (SEQ ID NO: 201) and $(X_1)_n$RQDDGAP$(X_7)_m$ (SEQ ID NO: 202), wherein $X_1$ and $X_7$ is cysteine and n and m, independently, are 0 or 1.

According to a preferred embodiment of the present invention the peptide is coupled to a pharmaceutically acceptable carrier, preferably KLH (Keyhole Limpet Hemocyanin).

The pharmaceutical formulation according to the present invention, which can be formulated as a vaccine for, e.g., subcutaneous, intradermal and/or intramuscular administration, may be used in the treatment of any kind of synucleinopathy.

The present invention is further illustrated in the following figures and examples, however, without being restricted thereto.

FIG. 1 shows the sequence of full length alpha-synuclein (SEQ ID NO: 1) (140aa; swiss prot entry: P37840) and the sequence used to create a monoclonal antibody for detection of full length alpha-synuclein as well as C-terminally truncated and modified versions thereof. The peptide at position 100-109 used for generation of the monoclonal antibody is underlined. The peptide (p4453) was coupled to a C at C-terminal position.

Figure 2:
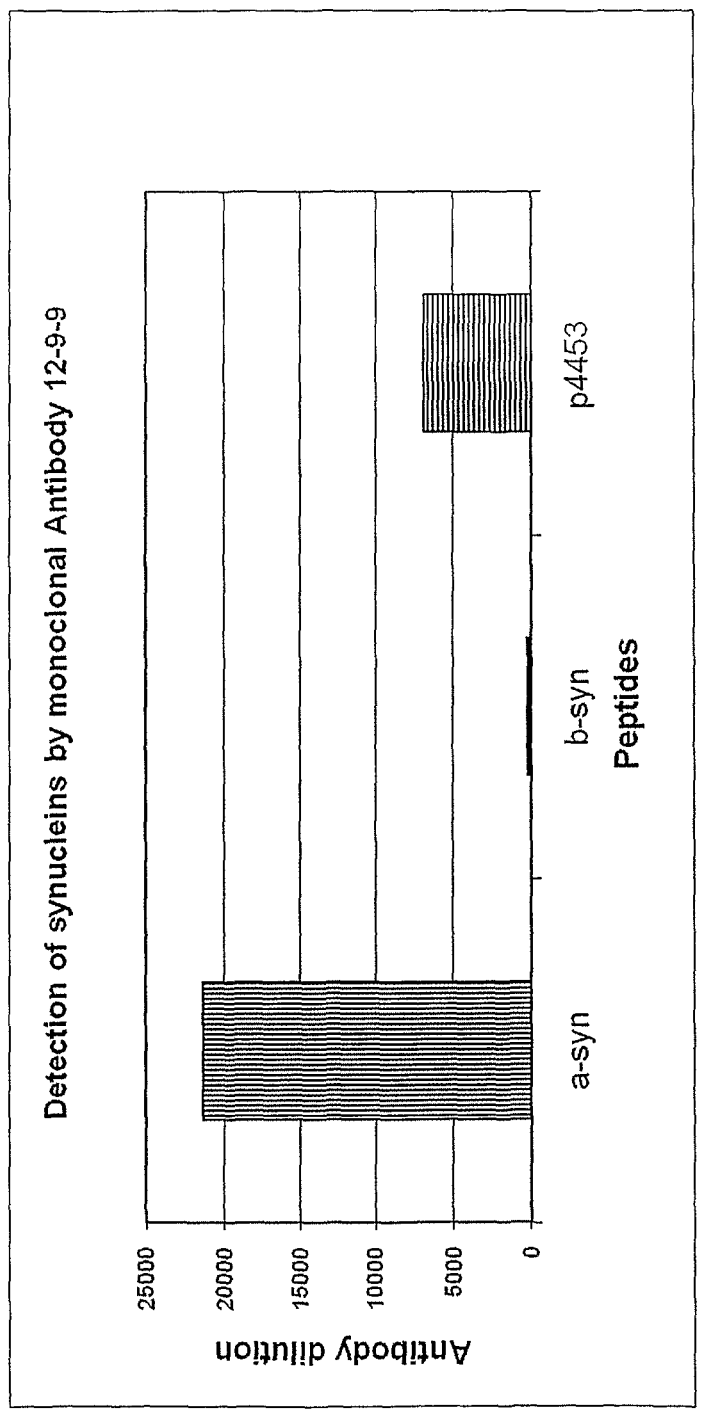
FIG. 2 shows detection of alpha-synuclein by ELISA using the generated monoclonal antibody specific for human alpha-synuclein at position 100-109. The monoclonal antibody 12-9-9 was generated and tested for its specificity to synucleins in ELISA. Alpha-synuclein (p4446) and p4453 the human epitope are detected. The negative control protein p4447 (beta-synuclein) is not detected.

FIG. 2 shows detection of alpha-synuclein by ELISA using the generated monoclonal antibody specific for human alpha-synuclein at position 100-109. The monoclonal antibody 12-9-9 was generated and tested for its specificity to synucleins in ELISA. Alpha-synuclein (p4446) and p4453 the human epitope are detected. The negative control protein p4447 (beta-synuclein) is not detected.

Figure 3:
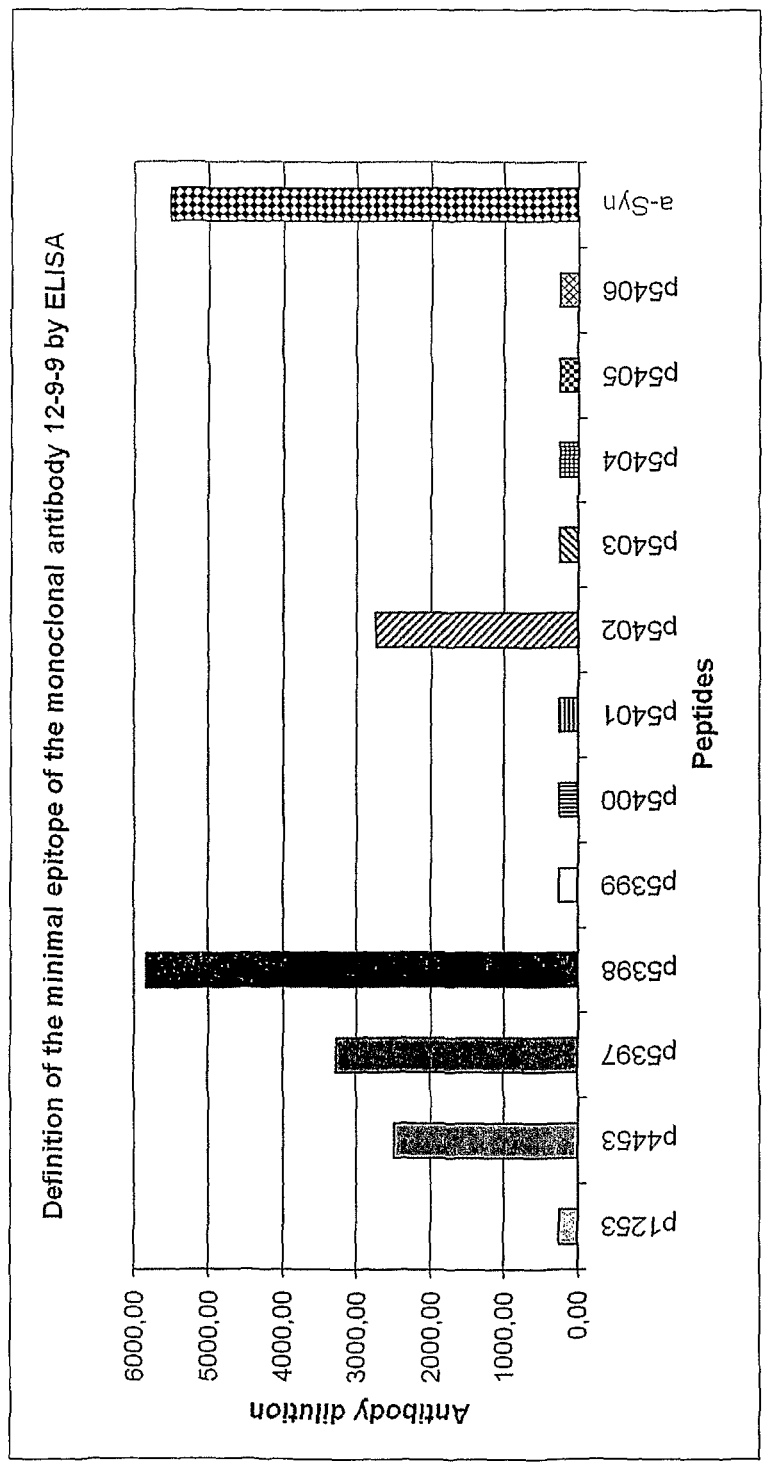
FIG. 3 shows the definition of the minimal epitope of the monoclonal antibody 12-9-9 by ELISA.

FIG. 3 shows the definition of the minimal epitope of the monoclonal antibody 12-9-9 by ELISA.

The peptides p4446 (alpha-synuclein), p4453 (human epitope used to create the antibody tested) are detected by the antibody. The original epitope p4453 was N- or C- terminally truncated and used for ELISA to define the minimal epitope required for specific binding. The peptides p5399 and p5403 lost binding to the monoclonal antibody 12-9-9. Thus the minimal sequence needed for binding of 12-9-9 is predicted as KNEEGAP (SEQ ID NO: 139) located at position 102-108 of alpha-synuclein, while truncation of one of the flanking amino acids abolished the binding. Data are presented in a linear scale.

FIG. 4 shows detection of epitopes and mimotopes by ELISA using a monoclonal specific for human alpha-synuclein at position 100-109. Alpha-Synuclein as well as the peptides p5436 (human minimal epitope) and the mimotopes p5439 are detected similarly by the monoclonal antibody 12-9-9. The mimotope p5440 is not detected, while mimotope p5444 is detected much weaker than the human epitope by the monoclonal antibody 12-9-9.

FIG. 5 shows the induction of immune response against alpha-synuclein after peptide immunization. Sera of immunized mice (p5436 to p5590) show titers against alpha-synuclein after 3 vaccinations. Sera of immunized mice (p5463 to p5466) do not detect alpha synuclein (Titers measured in ELISA are around or below 1:50 half-max). Class of immunogenicity was defined as follows: Class 2: peptides inducing an immune response with OD halfmax higher than 1:1000. Class 1: peptides inducing an immune response with OD halfmax between 1000 and 51. Class 0: peptides inducing no or an very low immune response with OD halfmax around 50 or lower.

EXAMPLES

To identify peptides and polypeptides which can be used to treat and/or prevent synucleopathies an antibody was used, which is able to detect the human alpha-synuclein-derived amino acid sequence LGKNEEGAPQ (SEQ ID NO: 203) (=original epitope, SEQ ID No. 3, p4453) and full length human alpha-synuclein (SEQ ID No. 1, p4446). It does not recognize human beta-synuclein (SEQ ID No. 2, p4447; accession number Q16143: mdvfmkglsm akegvvaaae ktkqgvteaa ektkegvlyv gsktregvvq gvasvaektk eqashlggav fsgagniaaa tglvkreefp tdlkpeevaq eaaeepliep lmepegesye dppqeeyqey epea). The antibody may be a monoclonal or polyclonal antibody preparation or any antibody part or derivative thereof and binds specifically to the LGKNEEGAPQ epitope (SEQ ID NO: 203) of human alpha-synuclein, i.e. it does bind to peptide and full length protein but does not bind to human beta-synuclein. The mimotopes are identified and further characterised with such monoclonal antibodies (detecting a sequence within amino acids 100-109 of the human alpha-synuclein protein) and peptide libraries.

Example 1

Generation of Monoclonal Antibodies to Specifically Detect Original Human Alpha-Synuclein Epitope LGKNEEGAPQC SEQ ID No. 3, p4453 and Human Alpha-Synuclein but not Human Beta-Synuclein A monoclonal antibody derived from the fusion "AFFiRiS 6": Balb/c mice (Charles River) were immunized with original alpha-synuclein epitope LGKNEEGAPQ-C (SEQ ID NO:3) coupled to BTG (bovine thyroglobuline) and CFA (complete Freund's adjuvant; first injection) as well as IFA (incomplete Freund's adjuvant; 3 booster injections) as adjuvant. LGKNEEGAPQ-peptide-specific (SEQ ID NO: 203) antibody-producing hybridomas are detected by ELISA (LGKNEEGAPQC-peptide-coated (SEQ ID NO: 3)ELISA plates). Human alpha-synuclein (recombinant protein, p4446) is used as positive control peptide: hybridomas recognizing the recombinant protein immobilized on ELISA plates are included because they are binding both peptide and full length alpha-synuclein specifically. Human beta-synuclein (recombinant protein, p4447) is used as negative control peptide: hybridomas recognizing both recombinant proteins immobilized on ELISA plates are excluded because they do not distinguish between the two different synuclein proteins. The Hybridoma clone (12-9-9; IgG1, kappa) was analysed for specific detection of the natural human alpha-synuclein epitope LGKNEEGAPQ. (SEQ ID NO: 203). 12-9-9 recognizes the injected epitope as well as full length alpha-synuclein protein (recombinant protein; obtained from rPeptide, Bogart, Ga., USA) in ELISA (see FIG. 2). It however does not detect beta-synuclein protein (recombinant protein, obtained from rPeptide, Bogart, Ga., USA) in ELISA (see FIG. 2). Subsequently, the minimal epitope required for binding of the antibody has been defined by ELISA using the peptides p4446, p4453, p5397, p5398, p5399, p5400, p5401, p5402, p5403, p5404, p5405, p5406 (see FIG. 3) and p5436 (see FIG. 4). p4446, p4453, p5397, p5398 and p5402 as well as p5436 retained full binding capacities whereas p5399, p5400, p5401, p5403, p5404, p5405 and p5406 lost binding to 12-9-9. Thus the minimal required epitope for binding has been defined as KNEEGAP (SEQ ID NO: 139).

Example 2

Phage Display, In Vitro Binding and Inhibition ELISA

Phage Display libraries used in this example were: Ph.D. 7: New England BioLabs E8102L (linear 7mer library), Ph.D. 12: New England BioLabs E8111L (linear 12mer library) and Ph.D. C7C: New England BioLabs E8120L (a disulfide-constrained heptapeptide library) Phage Display was done according to manufacturer's protocol. After 2 or 3 subsequent rounds of panning, single phage clones were picked and phage supernatants were subjected to ELISA on plates coated with the antibody that was used for the panning procedure. Phage clones that were positive in this ELISA (strong signal for the target, but no signal for unspecific control) were sequenced. From DNA sequences, peptide sequences were deduced. These peptides were synthesized and characterised in binding and inhibition ELISA. To some peptides additional AA were attached to the C-terminus. Additionally, some novel mimotopes were created by combining sequence information from mimotopes identified in the screen. Both groups containing newly designed mimotopes were used to support the identification of a consensus sequence for a mimotope vaccination.

1. In vitro binding assay (ELISA)

Peptides derived from Phage Display as well as N-terminally truncated variants thereof were coupled to BSA and bound to ELISA plates (1 µM) and subsequently incubated with the monoclonal antibody that was used for the screening procedure to analyse binding capacity of identified peptides (see FIG. 4).

2. In vitro inhibition assay (ELISA)

Different amounts of peptides (concentrations ranging from 400 µg/ml to 3 µg/ml (serial dilutions), derived from Phage Display were incubated with the monoclonal antibody that was used for the screening procedure. Peptides diminishing subsequent binding of the antibody to the original human alpha-synuclein epitope (p5436) and the human alpha-synuclein protein (p4446) coated on ELISA plates were considered as inhibiting in this assay.

Example 3

In Vivo Testing of Mimotopes: Analysis of Immunogenicity

1. In vivo testing of mimotopes

Inhibiting as well as non-inhibiting peptides were coupled to KLH and injected into mice (wildtype C57/B16 or BalbC mice; subcutaneous injection into the flank) together with an appropriate adjuvant (aluminium hydroxide). Animals were vaccinated 3 times in biweekly intervals and sera were taken biweekly as well. Titers to injected peptides as well as to an irrelevant peptide were determined with every serum. Titers against the recombinant human alpha-synuclein protein and recombinant human beta-synuclein were determined starting with Serum 2 respectively. In general sera were analysed by reaction against peptides coupled to Bovine Serum Albumin (BSA) and recombinant full length proteins which were immobilised on ELISA plates. Titers were determined using anti mouse IgG specific antibodies. For examples of immunogenicity against injected peptide and alpha-synuclein see Table 5 and Table 6.

2. Results

2.1. Identification of an alpha-synuclein specific mAB:

FIG. 2 depicts the characterisation of the alpha-synuclein specific monoclonal antibody 12-9-9 (IgG1, kappa) derived from fusion Affiris 6.

2.2. Screening for alpha-synuclein specific Mimotopes:

2.2.1. Phage Display PhD 7, PhD12 and PhD C7C and mutational Screen

2.2.1.1. Screening with monoclonal antibody directed against LGKNEEGAPQ (SEQ ID NO: 203)

By screening of PhD 7, PhD12 and PhD C7C phage display libraries and selective displacement of single amino acids a total of 60 sequences was identified (see Table 1; ID18-77). Table 1 shows examples all peptides used.

| SEQ ID | peptide No | sequence |
|---|---|---|
| 1 | p4446 | Alpha-synuclein (FIG. 1; P37840) |
| 2 | p4447 | Beta-Synuclein; Q16143 |
| 3 | p4453 | LGKNEEGAPQC |
| 4 | p4454 | MGKGEEGYPQC |
| 5 | p5397 | GKNEEGAPQC |
| 6 | p5398 | KNEEGAPQC |
| 7 | p5399 | NEEGAPQC |
| 8 | p5400 | EEGAPQC |
| 9 | p5401 | EGAPQC |
| 10 | p5402 | LGKNEEGAPC |
| 11 | p5403 | LGKNEEGAC |
| 12 | p5404 | LGKNEEGC |
| 13 | p5405 | LGKNEEC |
| 14 | p5406 | LGKNEC |
| 15 | p5435 | CKNEEGAP |
| 16 | p5436 | KNEEGAPC |
| 17 | p1253 | DAEFRHDSGY-C |
| 18 | p5437 | ANEEGAPC |
| 19 | p5438 | KAEEGAPC |
| 20 | p5439 | KNAEGAPC |
| 21 | p5440 | KNEAGAPC |
| 22 | p5441 | KNEEAAPC |
| 23 | p5442 | KNEEGAAC |
| 24 | p5443 | RNEEGAPC |
| 25 | p5444 | HNEEGAPC |
| 26 | p5445 | KNDEGAPC |
| 27 | p5446 | KNEDGAPC |
| 28 | p5447 | KQEEGAPC |
| 29 | p5448 | KSEEGAPC |
| 30 | p5449 | KNDDGAPC |
| 31 | p5461 | KPSFKNEC |
| 32 | p5462 | QPSFAMEC |
| 33 | p5463 | SPSFKQEC |
| 34 | p5464 | TPSWKGEC |
| 35 | p5465 | DPSFALEC |
| 36 | p5466 | LPSFRLEC |
| 37 | p5467 | EPNSRMDC |
| 38 | p5468 | QPSSKLDC |
| 39 | p5469 | HIHQSKFFDAPPC |
| 40 | p5547 | QASFAMEC |
| 41 | p5548 | TASWKGEC |
| 42 | p5549 | QASSKLDC |
| 43 | p5550 | QPAFAMEC |
| 44 | p5551 | TPAWKGEC |
| 45 | p5552 | QPASKLDC |
| 46 | p5553 | QPSFAMAC |
| 47 | p5554 | TPSWKGAC |
| 48 | p5555 | QPSSKLAC |
| 49 | p5556 | APSWKGEC |
| 50 | p5557 | TPSAKGEC |
| 51 | p5558 | TPSWAGEC |
| 52 | p5559 | TPSWKAEC |
| 53 | p5560 | CTPSWKGE |
| 54 | p5587 | RNDEGAPC |
| 55 | p5588 | RNEDGAPC |
| 56 | p5589 | RQEEGAPC |
| 57 | p5590 | RSEEGAPC |
| 58 | p5591 | ANDEGAPC |
| 59 | p5592 | ANEDGAPC |
| 60 | p5593 | HSEEGAPC |
| 61 | p5594 | ASEEGAPC |
| 62 | p5595 | HNEDGAPC |
| 63 | p5596 | HNDEGAPC |
| 64 | p5597 | RNAEGAPC |
| 65 | p5598 | HNAEGAPC |
| 66 | p5599 | KSAEGAPC |
| 67 | p5600 | KSDEGAPC |
| 68 | p5601 | KSEDGAPC |

-continued

| SEQ ID | peptide No | sequence |
|---|---|---|
| 69 | p5602 | RQDEGAPC |
| 70 | p5603 | RQEDGAPC |
| 71 | p5604 | HSAEGAPC |
| 72 | p5605 | RSAEGAPC |
| 73 | p5606 | RSDEGAPC |
| 74 | p5607 | RSEDGAPC |
| 75 | p5608 | HSDEGAPC |
| 76 | p5609 | HSEDGAPC |
| 77 | p5610 | RQDDGAPC |

Table 2 shows examples of peptides and their binding capicity as compared to the original eptide.

TABLE 2

Examples of alpha-synuclein epi- and mimotopes binding to the monoclonal Antibody 12-9-9

| internal number | Sequence | SEQ ID NO: | Binding | remark |
|---|---|---|---|---|
| p5435 | CKNEEGAP | 15 | 2 | original |
| p5436 | KNEEGAPC | 16 | 2 | original |
| p5437 | ANEEGAPC | 18 | 2 | mimotope |
| p5438 | KAEEGAPC | 19 | 1 | mimotope |
| p5439 | KNAEGAPC | 20 | 2 | mimotope |
| p5443 | RNEEGAPC | 24 | 2 | mimotope |
| p5444 | HNEEGAPC | 25 | 2 | mimotope |
| p5445 | KNDEGAPC | 26 | 2 | mimotope |
| p5446 | KNEDGAPC | 27 | 2 | mimotope |
| p5447 | KQEEGAPC | 28 | 2 | mimotope |
| p5448 | KSEEGAPC | 29 | 2 | mimotope |
| p5449 | KNDDGAPC | 30 | 2 | mimotope |
| p5398 | KNEEGAPQC | 6 | 2 | original |
| p5402 | LGKNEEGAPC | 10 | 2 | original |
| p5397 | GKNEEGAPQC | 5 | 2 | original |
| p4454 | MGKGEEGYPQC | 4 | 2 | original mouse |
| p4453 | LGKNEEGAPQC | 3 | 2 | original |
| p5461 | KPSFKNEC | 31 | 2 | mimotope |
| p5462 | QPSFAMEC | 32 | 2 | mimotope |
| p5463 | SPSFKQEC | 33 | 2 | mimotope |
| p5464 | TPSWKGEC | 34 | 2 | mimotope |
| p5465 | DPSFALEC | 35 | 2 | mimotope |
| p5466 | LPSFRLEC | 36 | 1 | mimotope |
| p5468 | QPSSKLDC | 38 | 2 | mimotope |
| p5547 | QASFAMEC | 40 | 1 | mimotope |
| p5548 | TASWKGEC | 41 | 2 | mimotope |
| p5549 | QASSKLDC | 42 | 1 | mimotope |
| p5551 | TPAWKGEC | 44 | 1 | mimotope |
| p5556 | APSWKGEC | 49 | 2 | mimotope |
| p5558 | TPSWAGEC | 51 | 2 | mimotope |
| p5560 | CTPSWKGE | 53 | 2 | mimotope |
| p5587 | --RNDEGAPC | 54 | 2 | mimotope |
| p5588 | --RNEDGAPC | 55 | 2 | mimotope |
| p5589 | --RQEEGAPC | 56 | 2 | mimotope |
| p5590 | --RSEEGAPC | 57 | 2 | mimotope |
| p5591 | --ANDEGAPC | 58 | 2 | mimotope |
| p5593 | --HSEEGAPC | 60 | 1 | mimotope |
| p5594 | --ASEEGAPC | 61 | 1 | mimotope |
| p5596 | --HNDEGAPC | 63 | 2 | mimotope |
| p5597 | --RNAEGAPC | 64 | 2 | mimotope |
| p5598 | --HNAEGAPC | 65 | 1 | mimotope |
| p5599 | --KSAEGAPC | 66 | 2 | mimotope |
| p5600 | --KSDEGAPC | 67 | 2 | mimotope |
| p5601 | --KSEDGAPC | 68 | 2 | mimotope |
| p5602 | --RQDEGAPC | 69 | 2 | mimotope |
| p5603 | --RQEDGAPC | 70 | 2 | mimotope |
| p5604 | --HSAEGAPC | 71 | 1 | mimotope |
| p5605 | --RSAEGAPC | 72 | 2 | mimotope |
| p5606 | --RSDEGAPC | 73 | 2 | mimotope |
| p5607 | --RSEDGAPC | 74 | 2 | mimotope |
| p5608 | --HSDEGAPC | 75 | 1 | mimotope |
| p5610 | --RQDDGAPC | 77 | 2 | mimotope |
| p4446 | | | 2 | α-Syn | the binding capacity is coded by the following code:
0: no binding to 12-9-9 detectable in ELISA
1: weak binding: binding of mimotope weaker compared to the minimal original sequence p5436
2: strong binding: binding of mimotope similar to the minimal original sequence p5436

2.3. In vitro characterisation of mimotopes identified in a screen (Phage Display and peptide screening) with a monoclonal antibody directed against alpha-synuclein:

FIGS. 2 and 3 show representative examples for binding and inhibition assays used to characterise mimotopes in vitro. Data obtained are summarised in Tables 2 and 3 respectively.

Table : Inhibition assay

TABLE 3

Inhibition assay
Alpha-synuclein mimotopes identified in this invention giving positive results in inhibition assays

| designation | Sequence | SEQ ID NO: | Competition | remark |
|---|---|---|---|---|
| p5435 | CKNEEGAP | 15 | 1 | original |
| p5436 | KNEEGAPC | 16 | 2 | original |
| p5439 | KNAEGAPC | 20 | 1 | mimotope |
| p5443 | RNEEGAPC | 24 | 2 | mimotope |
| p5445 | KNDEGAPC | 26 | 2 | mimotope |
| p5446 | KNEDGAPC | 27 | 1 | mimotope |
| p5448 | KSEEGAPC | 29 | 1 | mimotope |
| p5449 | KNDDGAPC | 30 | 1 | mimotope |
| p5398 | KNEEGAPQC | 6 | 2 | original |
| p5402 | LGKNEEGAPC | 10 | 2 | original |
| p5397 | GKNEEGAPQC | 5 | 2 | original mouse |
| p5464 | TPSWKGEC | 34 | 1 | mimotope |
| p5548 | TASWKGEC | 41 | 1 | mimotope |
| p5556 | APSWKGEC | 49 | 1 | mimotope |
| p5557 | TPSAKGEC | 50 | 1 | mimotope |
| p5587 | RNDEGAPC | 54 | 2 | mimotope |
| p5588 | RNEDGAPC | 55 | 1 | mimotope |
| p5590 | RSEEGAPC | 57 | 1 | mimotope |
| p5597 | RNAEGAPC | 64 | 1 | mimotope |
| p5600 | KSDEGAPC | 67 | 1 | mimotope |
| p5602 | RQDEGAPC | 69 | 1 | mimotope |
| p5603 | RQEDGAPC | 70 | 1 | mimotope |

Legend to Table 3: the competition capacity is coded by the following code:
0: no competition of 12-9-9 detectable in ELISA
1: weak competition: competition of mimotope weaker compared to the minimal original sequence p5436
2: strong competition: competition of mimotope similar to the minimal original sequence p5436

TABLE 4

Non-Mimotope peptides and proteins:

| SEQ ID No. | designation | sequence |
|---|---|---|
| 1 | p4446 | Alpha-synuclein |
| 2 | p4447 | Beta-Synuclein |
| 3 | p4453 | LGKNEEGAPQC |
| 4 | p4454 | MGKGEEGYPQC |
| 5 | p5397 | GKNEEGAPQC |
| 6 | p5398 | KNEEGAPQC |
| 7 | p5399 | NEEGAPQC |
| 8 | p5400 | EEGAPQC |
| 9 | p5401 | EGAPQC |
| 10 | p5402 | LGKNEEGAPC |
| 11 | p5403 | LGKNEEGAC |
| 12 | p5404 | LGKNEEGC |
| 13 | p5405 | LGKNEEC |
| 14 | p5406 | LGKNEC |
| 15 | p5435 | CKNEEGAP |
| 16 | p5436 | KNEEGAPC |
| 17 | p1253 | DAEFRHDSGY-C |

2.4. In vivo characterisation of mimotopes identified in screening Phage Display Libraries with a monoclonal antibody directed against alpha-synuclein:

Female C57/B16 mice or BalbC, 5-6 mice per group, were subcutaneously immunized with 30 µg peptide coupled to KLH. Control groups were injected with PBS or the original epitope. As adjuvant alum was used. The peptides administered were all able to bind to monoclonal antibodies specifically binding aa100-109 of human alpha-synuclein although some of the peptides did inhibit the binding of the original epitope to its parental antibody in vitro only weakly (in an in vitro inhibition assay). The in vitro ELISA assay to determine the antibody titer was performed with sera of single mice (see Tab. 5) after each vaccination in a two week interval. The wells of the ELISA plate were coated with mimotope-BSA conjugates. The positive control was performed by reaction of the parental antibody with the respective mimotope-BSA conjugate. The detection was performed with anti-mouse IgG. Additionally, recombinant proteins were immobilised on ELISA plates and sera reacted accordingly. For all mimotopes tested in C57/B16 mice or BalbC, antibodies reacting to the individual injected peptide could be detected after repeated vaccination. Although not all mice induced higher titer against alpha-synuclein (see tab. 5 for examples).

TABLE 5

Induction of immune response is indicated by the titer against injected peptide (p4446). Titer was measured by ELISA and indicated as OD halfmax.

| designation | Sequence | SEQ ID NO: | Titer in animals OD halfmax injected pep. | remark |
|---|---|---|---|---|
| p5436 | KNEEGAPC | 16 | 10000 | original |
| p5439 | KNAEGAPC | 20 | 8000 | mimotope |
| p5443 | RNEEGAPC | 24 | 9000 | mimotope |
| p5445 | KNDEGAPC | 26 | 26000 | mimotope |
| p5402 | LGKNEEGAPC | 10 | 20000 | original |
| p4454 | MGKGEEGYPQC | 4 | 17000 | original mouse |

TABLE 6 class of immunogenicity of mimotopes against a Syn

| designation | sequence | SEQ ID NO: | class of immunogenicity: a Syn | remark |
|---|---|---|---|---|
| p5402 | LGKNEEGAP-C | 10 | 2 | original |
| p5436 | KNEEGAPC | 16 | 2 | original |
| p5445 | KNDEGAPC | 26 | 2 | mimotope |
| p5443 | RNEEGAPC | 24 | 1 | mimotope |
| p5587 | RNDEGAPC | 54 | 1 | mimotope |
| p5439 | KNAEGAPC | 20 | 1 | mimotope |
| p5600 | KSDEGAPC | 67 | 1 | mimotope |
| p4454 | MGKGEEGYPQC | 4 | 1 | original mouse |
| p5597 | RNAEGAPC | 64 | 1 | mimotope |
| p5590 | RSEEGAPC | 57 | 1 | mimotope |
| p5463 | SPSFKQEC | 33 | 0 | mimotope |
| p5556 | APSWKGEC | 49 | 0 | mimotope |
| p5462 | QPSFAMEC | 32 | 0 | mimotope |
| p5464 | TPSWKGEC | 34 | 0 | mimotope |
| p5468 | QPSSKLDC | 38 | 0 | mimotope |
| p5461 | KPSFKNEC | 31 | 0 | mimotope |
| p5465 | DPSFALEC | 35 | 0 | mimotope |
| p5466 | LPSFRLEC | 36 | 0 | mimotope |

Class of immunogenicity:
peptides were ranked according to their capacity to induce an immune response
2: peptides inducing an immune response with OD halfmax higher than 1000.
1: peptides inducing an immune response with OD halfmax between 1000 and 51.
0: peptides inducing no immune response or a very low immune response with OD halfmax around 50 or lower.

The invention claimed is:

1. A composition comprising a peptide or polypeptide comprising the amino acid sequence $$(X_1)_n X_2 X_3 X_4 X_5 G X_6 P(X_7)_m \text{(SEQ ID NO: 78)} \quad \text{(Formula I)},$$

wherein $X_1$ is any amino acid residue, $X_2$ is an amino acid residue selected from the group consisting of lysine (K), arginine (R), alanine (A) and histidine (H), $X_3$ is an amino acid residue selected from the group consisting of asparagine (N), glutamine (Q), serine (S), glycine (G) and alanine (A), $X_4$ is an amino acid residue selected from the group consisting of glutamic acid (E), aspartic acid (D) and alanine (A), $X_5$ is an amino acid residue selected from the group consisting of glutamic acid (E) and aspartic acid (D), $X_6$ is an amino acid residue selected from the group consisting of alanine (A) and tyrosine (Y), $X_7$ is any amino acid residue, n and m, independently, are 0 or an integer of more than 0, and wherein the amino acid sequence according to Formula I is not identical with, or does not comprise the 7-mer polypeptide fragment of alpha-synuclein having the amino acid sequence KNEEGAP (SEQ ID NO: 139) and wherein the peptide or polypeptide does not comprise the amino acid sequence of formula I wherein $X_2$ is K, $X_3$ is G, $X_4$ is E, $X_5$ is E, $X_6$ is Y and $X_7$ is P, said at least one peptide or polypeptide having a binding capacity to an antibody which is specific for an epitope of alpha-synuclein comprising the amino acid sequence KNEEGAP (SEQ ID NO: 139), suitable for use in preventing and/or treating synucleinopathies.

2. The composition according to claim 1, wherein $X_2$ is an amino acid residue selected from the group consisting of lysine (K) and arginine (R) and/or $X_6$ is alanine (A) (SEQ ID NO: 204).

3. The composition according to claim 1 wherein the peptide or polypeptide comprises an amino acid sequence selected from the group consisting of $(X_1)_n$KNDEGAP$(X_7)_m$ (SEQ ID NO: 87), $(X_1)_n$ANEEGAP$(X_7)_m$(SEQ ID NO: 79), $(X_1)_n$KAEEGAP$(X_7)_m$(SEQ ID NO: 80), $(X_1)_n$KNAEGAP$(X_7)_m$(SEQ ID NO: 81), $(X_1)_n$RNEEGAP$(X_7)_m$, (SEQ ID NO: 85), $(X_1)_n$HNEEGAP$(X_7)_m$(SEQ ID NO: 86), $(X_1)_n$KNEDGAP$(X_7)_m$, (SEQ ID NO: 88), $(X_1)_n$KQEEGAP$(X_7)_m$ (SEQ ID NO: 89), $(X_1)_n$KSEEGAP$(X_7)_m$, (SEQ ID NO: 90), $(X_1)_n$KNDDGAP $(X_7)_m$, (SEQ ID NO: 91), $(X_1)_n$ RNDEGAP$(X_7)_m$, (SEQ ID NO: 115), $(X_1)_n$RNEDGAP$(X_7)_m$(SEQ ID NO: 116), $(X_1)_n$RQEEGAP$(X_7)_m$, (SEQ ID NO: 117), $(X_1)_n$RSEEGAP$(X_7)_m$(SEQ ID NO: 118), $(X_1)_n$ANDEGAP $(X_7)_m$(SEQ ID NO: 119), $(X_1)_n$ANEDGAP$(X_7)_m$ (SEQ ID NO: 120), $(X_1)_n$HSEEGAP$(X_7)_m$, (SEQ ID NO: 121), $(X_1)_n$ ASEEGAP$(X_7)_m$(SEQ ID NO: 122), $(X_1)_n$ HNEDGAP $(X_7)_m$, (SEQ ID NO: 123), $(X_1)_n$HNDEGAP$(X_7)_m$(SEQ ID NO: 124), $(X_1)_n$RNAEGAP$(X_7)_m$, (SEQ ID NO: 125), $(X_1)_n$ HNAEGAP$(X_7)_m$(SEQ ID NO: 126), $(X_1)_n$ KSAEGAP $(X_7)_m$ (SEQ ID NO: 127), $(X_1)_n$KSDEGAP$(X_7)_m$ (SEQ ID NO: 128), $(X_1)_n$KSEDGAP$(X_7)_m$(SEQ ID NO: 129), $(X_1)_n$ RQDEGAP$(X_7)_m$(SEQ ID NO: 141), $(X_1)_n$ RQEDGAP $(X_7)_m$ (SEQ ID NO: 131), $(X_1)_n$HSAEGAP$(X_7)_m$, (SEQ ID NO: 132), $(X_1)_n$RSAEGAP$(X_7)_m$(SEQ ID NO: 133), $(X_1)_n$ RSDEGAP$(X_7)_m$(SEQ ID NO: 134), $(X_1)_n$RSEDGAP$(X_7)_m$ (SEQ ID NO: 135),$(X_1)_n$HSDEGAP$(X_7)_m$(SEQ ID NO: 136), $(X_1)_n$HSEDGAP$(X_7)_m$, (SEQ ID NO: 137), and $(X_1)_n$ RQDDGAP$(X_7)_m$, (SEQ ID NO: 138).

4. The composition according to claim 1, wherein n and/or m are 1, and $X_1$ and/or $X_7$ are cysteine (C).

5. The composition according to claim 1, wherein the peptide or polypeptide consists of 7 to 30 amino acid residues.

6. The composition according to claim 1, wherein the synucleinopathy is selected from the group consisting of Lewy Body Disorders (LBDs), Multiple System Atrophy (MSA) and Neurodegeneration with Brain Iron Accumulation type I (NBIA Type I).

7. The composition according to claim 1, wherein the at least one peptide or polypeptide is coupled to a pharmaceutically acceptable carrier.

8. The composition according to claim 1, wherein the at least one peptide or polypeptide is formulated for intravenous, subcutaneous, intradermal or intramuscular administration.

9. The composition according to claim 1, wherein the at least one peptide or polypeptide is formulated with an adjuvant.

10. The composition according to claim 1, comprising 0.1 ng to 10 mg of the at least one peptide or polypeptide.

11. A peptide having an amino acid sequence selected from the group consisting of $(X_1)_n$KNDEGAP$(X_7)_m$(SEQ ID NO: 143), $(X_1)_n$ANEEGAP$(X_7)_m$(SEQ ID NO: 144), $(X_1)_n$KAEEGAP$(X_7)_m$(SEQ ID NO: 145), $(X_1)_n$KNAEGAP$(X_7)_m$ (SEQ ID NO: 146), $(X_1)_n$RNEEGAP$(X_7)_m$ (SEQ ID NO: 150), $(X_1)_n$HNEEGAP$(X_7)_m$ (SEQ ID NO: 151), $(X_1)_n$KNEDGAP$(X_7)_m$ (SEQ ID NO: 152), $(X_1)_n$KQEEGAP$(X_7)_m$ (SEQ ID NO: 153), $(X_1)_n$KSEEGAP$(X_7)_m$(SEQ ID NO: 154), $(X_1)_n$KNDDGAP$(X_7)_m$(SEQ ID NO: 155), $(X_1)_n$RNDEGAP$(X_7)_m$ (SEQ ID NO: 179), $(X_1)_n$RNEDGAP$(X_7)_m$ (SEQ ID NO: 180), $(X_1)_n$RQEEGAP$(X_7)_m$ (SEQ ID NO: 181), $(X_1)_n$RSEEGAP$(X_7)_m$ (SEQ ID NO: 182), $(X_1)_n$ANDEGAP$(X_7)_m$ (SEQ ID NO: 183), $(X_1)_n$ANEDGAP$(X_7)_m$ (SEQ ID NO: 184), $(X_1)_n$HSEEGAP$(X_7)_m$ (SEQ ID NO: 185), $(X_1)_n$ASEEGAP$(X_7)_m$(SEQ ID NO: 186), $(X_1)_n$HNEDGAP$(X_7)_m$(SEQ ID NO: 187), $(X_1)_n$HNDEGAP$(X_7)_m$ (SEQ ID NO: 188), $(X_1)_n$RNAEGAP$(X_7)_m$ (SEQ ID NO: 189), $(X_1)_n$HNAEGAP$(X_7)_m$(SEQ ID NO: 190), $(X_1)_n$KSAEGAP$(X_7)_m$ (SEQ ID NO: 191), $(X_1)_n$KSDEGAP$(X_7)_m$ (SEQ ID NO: 192), $(X_1)_n$KSEDGAP$(X_7)_m$ (SEQ ID NO: 193), $(X_1)_n$RQDEGAP$(X_7)_m$ (SEQ ID NO: 194), $(X_1)_n$RQEDGAP$(X_7)_m$ (SEQ ID NO: 195), $(X_1)_n$HSAEGAP$(X_7)_m$ (SEQ ID NO: 196), $(X_1)_n$RSAEGAP$(X_7)_m$ (SEQ ID NO: 197), $(X_1)_n$RSDEGAP$(X_7)$, (SEQ ID NO: 198), $(X_1)_n$RSEDGAP$(X_7)_m$ (SEQ ID NO: 199), $(X_1)_n$HSDEGAP$(X_7)_m$ (SEQ ID NO: 200), $(X_1)_n$HSEDGAP$(X_7)$, (SEQ ID NO: 201) and $(X_1)_n$RQDDGAP$(X_7)_m$ (SEQ ID NO: 202), wherein $X_1$ and $X_7$ are each cysteine and n and m, independently, are 0 or 1.

\* \* \* \* \*

SEQUENCE LISTING

<160> NUMBER OF SEQ ID NOS: 204

<210> SEQ ID NO 1
<211> LENGTH: 140
<212> TYPE: PRT
<213> ORGANISM: Homo sapiens

<400> SEQUENCE: 1

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
```

```
                65                  70                  75                  80
Thr Val Glu Gly Ala Gly Ser Ile Ala Ala Thr Gly Phe Val Lys
                    85                  90                  95
Lys Asp Gln Leu Gly Lys Asn Glu Glu Gly Ala Pro Gln Glu Gly Ile
                    100                 105                 110
Leu Glu Asp Met Pro Val Asp Pro Asp Asn Glu Ala Tyr Glu Met Pro
                115                 120                 125
Ser Glu Glu Gly Tyr Gln Asp Tyr Glu Pro Glu Ala
            130                 135                 140

<210> SEQ ID NO 2
<211> LENGTH: 134
<212> TYPE: PRT
<213> ORGANISM: Homo sapiens

<400> SEQUENCE: 2

Met Asp Val Phe Met Lys Gly Leu Ser Met Ala Lys Glu Gly Val Val
1               5                   10                  15
Ala Ala Ala Glu Lys Thr Lys Gln Gly Val Thr Glu Ala Ala Glu Lys
                20                  25                  30
Thr Lys Glu Gly Val Leu Tyr Val Gly Ser Lys Thr Arg Glu Gly Val
            35                  40                  45
Val Gln Gly Val Ala Ser Val Ala Glu Lys Thr Lys Glu Gln Ala Ser
        50                  55                  60
His Leu Gly Gly Ala Val Phe Ser Gly Ala Gly Asn Ile Ala Ala Ala
65                  70                  75                  80
Thr Gly Leu Val Lys Arg Glu Gly Phe Pro Thr Asp Leu Lys Pro Glu
                85                  90                  95
Glu Val Ala Gln Glu Ala Ala Glu Glu Pro Leu Ile Glu Pro Leu Met
                100                 105                 110
Glu Pro Glu Gly Glu Ser Tyr Glu Asp Pro Pro Gln Glu Glu Tyr Gln
            115                 120                 125
Glu Tyr Glu Pro Glu Ala
        130

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      fragment of human alpha-synuclein peptide

<400> SEQUENCE: 3

Leu Gly Lys Asn Glu Glu Gly Ala Pro Gln Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 4

Met Gly Lys Gly Glu Glu Gly Tyr Pro Gln Cys
1               5                   10

<210> SEQ ID NO 5
```

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 5

Gly Lys Asn Glu Glu Gly Ala Pro Gln Cys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 6

Lys Asn Glu Glu Gly Ala Pro Gln Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 7

Asn Glu Glu Gly Ala Pro Gln Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 8

Glu Glu Gly Ala Pro Gln Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 9

Glu Gly Ala Pro Gln Cys
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 10

Leu Gly Lys Asn Glu Glu Gly Ala Pro Cys
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 11

Leu Gly Lys Asn Glu Glu Gly Ala Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 12

Leu Gly Lys Asn Glu Glu Gly Cys
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 13

Leu Gly Lys Asn Glu Glu Cys
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 14

Leu Gly Lys Asn Glu Cys
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 15

Cys Lys Asn Glu Glu Gly Ala Pro
1               5

<210> SEQ ID NO 16
<211> LENGTH: 8
<212> TYPE: PRT
<213> ORGANISM: Artificial Sequence
<220> FEATURE:

```
<223> OTHER INFORMATION: Description of Artificial Sequence: Synthetic
      mimotope peptide

<400> SEQUENCE: 16

Lys Asn Glu Glu Gly Ala Pro Cys
1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 17

Asp Ala Glu Phe Arg His Asp Ser Gly Tyr Cys
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 18

Ala Asn Glu Glu Gly Ala Pro Cys
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 19

Lys Ala Glu Glu Gly Ala Pro Cys
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 20

Lys Asn Ala Glu Gly Ala Pro Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 21

Lys Asn Glu Ala Gly Ala Pro Cys
1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 22

Lys Asn Glu Glu Ala Ala Pro Cys
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 23

Lys Asn Glu Glu Gly Ala Ala Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 24

Arg Asn Glu Glu Gly Ala Pro Cys
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 25

His Asn Glu Glu Gly Ala Pro Cys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 26

Lys Asn Asp Glu Gly Ala Pro Cys
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 27
```

```
Lys Asn Glu Asp Gly Ala Pro Cys
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 28

Lys Gln Glu Glu Gly Ala Pro Cys
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 29

Lys Ser Glu Glu Gly Ala Pro Cys
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 30

Lys Asn Asp Asp Gly Ala Pro Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 31

Lys Pro Ser Phe Lys Asn Glu Cys
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 32

Gln Pro Ser Phe Ala Met Glu Cys
1               5

<210> SEQ ID NO 33
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      mimotope peptide

<400> SEQUENCE: 33

Ser Pro Ser Phe Lys Gln Glu Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 34

Thr Pro Ser Trp Lys Gly Glu Cys
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 35

Asp Pro Ser Phe Ala Leu Glu Cys
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 36

Leu Pro Ser Phe Arg Leu Glu Cys
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 37

Glu Pro Asn Ser Arg Met Asp Cys
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 38

Gln Pro Ser Ser Lys Leu Asp Cys
1               5
```

```
<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 39

His Ile His Gln Ser Lys Phe Phe Asp Ala Pro Pro Cys
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 40

Gln Ala Ser Phe Ala Met Glu Cys
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 41

Thr Ala Ser Trp Lys Gly Glu Cys
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 42

Gln Ala Ser Ser Lys Leu Asp Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 43

Gln Pro Ala Phe Ala Met Glu Cys
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide
```

```
<400> SEQUENCE: 44

Thr Pro Ala Trp Lys Gly Glu Cys
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 45

Gln Pro Ala Ser Lys Leu Asp Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 46

Gln Pro Ser Phe Ala Met Ala Cys
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 47

Thr Pro Ser Trp Lys Gly Ala Cys
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 48

Gln Pro Ser Ser Lys Leu Ala Cys
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 49

Ala Pro Ser Trp Lys Gly Glu Cys
1               5

<210> SEQ ID NO 50
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      mimotope peptide

<400> SEQUENCE: 50

Thr Pro Ser Ala Lys Gly Glu Cys
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 51

Thr Pro Ser Trp Ala Gly Glu Cys
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 52

Thr Pro Ser Trp Lys Ala Glu Cys
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 53

Cys Thr Pro Ser Trp Lys Gly Glu
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 54

Arg Asn Asp Glu Gly Ala Pro Cys
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 55

Arg Asn Glu Asp Gly Ala Pro Cys
1               5
```

```
<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 56

Arg Gln Glu Glu Gly Ala Pro Cys
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 57

Arg Ser Glu Glu Gly Ala Pro Cys
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 58

Ala Asn Asp Glu Gly Ala Pro Cys
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 59

Ala Asn Glu Asp Gly Ala Pro Cys
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 60

His Ser Glu Glu Gly Ala Pro Cys
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide
```

```
<400> SEQUENCE: 61

Ala Ser Glu Glu Gly Ala Pro Cys
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 62

His Asn Glu Asp Gly Ala Pro Cys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 63

His Asn Asp Glu Gly Ala Pro Cys
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 64

Arg Asn Ala Glu Gly Ala Pro Cys
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 65

His Asn Ala Glu Gly Ala Pro Cys
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 66

Lys Ser Ala Glu Gly Ala Pro Cys
1               5

<210> SEQ ID NO 67
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 67

Lys Ser Asp Glu Gly Ala Pro Cys
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 68

Lys Ser Glu Asp Gly Ala Pro Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 69

Arg Gln Asp Glu Gly Ala Pro Cys
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 70

Arg Gln Glu Asp Gly Ala Pro Cys
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 71

His Ser Ala Glu Gly Ala Pro Cys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 72

Arg Ser Ala Glu Gly Ala Pro Cys
```

```
<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 73

Arg Ser Asp Glu Gly Ala Pro Cys
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 74

Arg Ser Glu Asp Gly Ala Pro Cys
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 75

His Ser Asp Glu Gly Ala Pro Cys
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 76

His Ser Glu Asp Gly Ala Pro Cys
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 77

Arg Gln Asp Asp Gly Ala Pro Cys
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (2)..(2)
<223> OTHER INFORMATION: Lys, Arg, Ala or His
<220> FEATURE:
<221> NAME/KEY: MOD_RES
<222> LOCATION: (3)..(3)
<223> OTHER INFORMATION: Asn, Gln, Ser, Gly or Ala
<220> FEATURE:
<221> NAME/KEY: MOD_RES
<222> LOCATION: (4)..(4)
<223> OTHER INFORMATION: Glu, Asp or Ala
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (7)..(7)
<223> OTHER INFORMATION: Ala or Tyr
<220> FEATURE:
<221> NAME/KEY: MOD_RES
<222> LOCATION: (9)..(9)
<223> OTHER INFORMATION: Any amino acid, preferably Cys, and this region
      may or may not be present
<220> FEATURE:
<223> OTHER INFORMATION: See specification as filed for detailed
      description of substitutions and preferred embodiments

<400> SEQUENCE: 78

Xaa Xaa Xaa Xaa Xaa Gly Xaa Pro Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 79

Xaa Ala Asn Glu Glu Gly Ala Pro Xaa
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
```

```
<222> LOCATION: (9)..(9)
<223> OTHER INFORMATION: Any amino acid, preferably Cys, and this region
      may or may not be present

<400> SEQUENCE: 80

Xaa Lys Ala Glu Glu Gly Ala Pro Xaa
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 81

Xaa Lys Asn Ala Glu Gly Ala Pro Xaa
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 82

Xaa Lys Asn Glu Ala Gly Ala Pro Xaa
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 83

Xaa Lys Asn Glu Glu Ala Ala Pro Xaa
```

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 84

Xaa Lys Asn Glu Glu Gly Ala Ala Xaa
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 85

Xaa Arg Asn Glu Glu Gly Ala Pro Xaa
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 86

Xaa His Asn Glu Glu Gly Ala Pro Xaa
1               5

<210> SEQ ID NO 87
<211> LENGTH: 9
<212> TYPE: PRT
<213> ORGANISM: Artificial Sequence

```
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 87

Xaa Lys Asn Asp Glu Gly Ala Pro Xaa
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 88

Xaa Lys Asn Glu Asp Gly Ala Pro Xaa
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 89

Xaa Lys Gln Glu Glu Gly Ala Pro Xaa
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
```

```
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 90

Xaa Lys Ser Glu Glu Gly Ala Pro Xaa
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 91

Xaa Lys Asn Asp Asp Gly Ala Pro Xaa
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 92

Xaa Lys Pro Ser Phe Lys Asn Glu Xaa
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present
```

```
<400> SEQUENCE: 93

Xaa Gln Pro Ser Phe Ala Met Glu Xaa
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 94

Xaa Ser Pro Ser Phe Lys Gln Glu Xaa
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 95

Xaa Thr Pro Ser Trp Lys Gly Glu Xaa
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 96

Xaa Asp Pro Ser Phe Ala Leu Glu Xaa
1               5

<210> SEQ ID NO 97
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 97

Xaa Leu Pro Ser Phe Arg Leu Glu Xaa
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 98

Xaa Glu Pro Asn Ser Arg Met Asp Xaa
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 99

Xaa Gln Pro Ser Ser Lys Leu Asp Xaa
1               5

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
```

<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (14)..(14)
<223> OTHER INFORMATION: Any amino acid, preferably Cys, and this region
      may or may not be present

<400> SEQUENCE: 100

Xaa His Ile His Gln Ser Lys Phe Phe Asp Ala Pro Pro Xaa
1               5                   10

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 101

Xaa Gln Ala Ser Phe Ala Met Glu Xaa
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 102

Xaa Thr Ala Ser Trp Lys Gly Glu Xaa
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)

```
<223> OTHER INFORMATION: Any amino acid, preferably Cys, and this region
      may or may not be present

<400> SEQUENCE: 103

Xaa Gln Ala Ser Ser Lys Leu Asp Xaa
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 104

Xaa Gln Pro Ala Phe Ala Met Glu Xaa
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 105

Xaa Thr Pro Ala Trp Lys Gly Glu Xaa
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 106

Xaa Gln Pro Ala Ser Lys Leu Asp Xaa
1               5
```

```
<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 107

Xaa Gln Pro Ser Phe Ala Met Ala Xaa
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 108

Xaa Thr Pro Ser Trp Lys Gly Ala Xaa
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 109

Xaa Gln Pro Ser Ser Lys Leu Ala Xaa
1               5

<210> SEQ ID NO 110
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 110

Xaa Ala Pro Ser Trp Lys Gly Glu Xaa
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 111

Xaa Thr Pro Ser Ala Lys Gly Glu Xaa
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 112

Xaa Thr Pro Ser Trp Ala Gly Glu Xaa
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
```

```
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 113

Xaa Thr Pro Ser Trp Lys Ala Glu Xaa
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 114

Xaa Thr Pro Ser Trp Lys Gly Glu Xaa
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 115

Xaa Arg Asn Asp Glu Gly Ala Pro Xaa
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 116
```

```
Xaa Arg Asn Glu Asp Gly Ala Pro Xaa
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 117

Xaa Arg Gln Glu Glu Gly Ala Pro Xaa
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 118

Xaa Arg Ser Glu Glu Gly Ala Pro Xaa
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 119

Xaa Ala Asn Asp Glu Gly Ala Pro Xaa
1               5

<210> SEQ ID NO 120
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 120

Xaa Ala Asn Glu Asp Gly Ala Pro Xaa
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 121

Xaa His Ser Glu Glu Gly Ala Pro Xaa
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 122

Xaa Ala Ser Glu Glu Gly Ala Pro Xaa
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
```

```
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 123

Xaa His Asn Glu Asp Gly Ala Pro Xaa
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 124

Xaa His Asn Asp Glu Gly Ala Pro Xaa
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 125

Xaa Arg Asn Ala Glu Gly Ala Pro Xaa
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
```

```
                      may or may not be present

<400> SEQUENCE: 126

Xaa His Asn Ala Glu Gly Ala Pro Xaa
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 127

Xaa Lys Ser Ala Glu Gly Ala Pro Xaa
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 128

Xaa Lys Ser Asp Glu Gly Ala Pro Xaa
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 129

Xaa Lys Ser Glu Asp Gly Ala Pro Xaa
1               5
```

```
<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 130

Arg Gln Asp Glu Gly Ala Pro
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 131

Xaa Arg Gln Glu Asp Gly Ala Pro Xaa
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 132

Xaa His Ser Ala Glu Gly Ala Pro Xaa
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
``` may or may not be present

<400> SEQUENCE: 133

Xaa Arg Ser Ala Glu Gly Ala Pro Xaa
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 134

Xaa Arg Ser Asp Glu Gly Ala Pro Xaa
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 135

Xaa Arg Ser Glu Asp Gly Ala Pro Xaa
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 136

Xaa His Ser Asp Glu Gly Ala Pro Xaa
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 137

Xaa His Ser Glu Asp Gly Ala Pro Xaa
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 138

Xaa Arg Gln Asp Asp Gly Ala Pro Xaa
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      fragment of human alpha-synuclein peptide

<400> SEQUENCE: 139

Lys Asn Glu Glu Gly Ala Pro
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 140

His His His His His His
1               5

<210> SEQ ID NO 141
<211> LENGTH: 9

```
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (9)..(9)
<223> OTHER INFORMATION: Any amino acid, preferably Cys, and this region
      may or may not be present

<400> SEQUENCE: 141

Xaa Arg Gln Asp Glu Gly Ala Pro Xaa
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (2)..(2)
<223> OTHER INFORMATION: Lys, Arg, Ala or His
<220> FEATURE:
<221> NAME/KEY: MOD_RES
<222> LOCATION: (3)..(3)
<223> OTHER INFORMATION: Asn, Gln, Ser, Gly or Ala
<220> FEATURE:
<221> NAME/KEY: MOD_RES
<222> LOCATION: (4)..(4)
<223> OTHER INFORMATION: Glu, Asp or Ala
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (7)..(7)
<223> OTHER INFORMATION: Ala or Tyr
<220> FEATURE:
<221> NAME/KEY: MOD_RES
<222> LOCATION: (9)..(9)
<223> OTHER INFORMATION: Any amino acid, preferably Cys, and this region
      may or may not be present
<220> FEATURE:
<223> OTHER INFORMATION: See specification as filed for detailed
      description of substitutions and preferred embodiments

<400> SEQUENCE: 142

Xaa Xaa Xaa Xaa Xaa Gly Xaa Pro Xaa
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
```

```
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 143

Cys Lys Asn Asp Glu Gly Ala Pro Cys
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 144

Cys Ala Asn Glu Glu Gly Ala Pro Cys
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 145

Cys Lys Ala Glu Glu Gly Ala Pro Cys
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 146

Cys Lys Asn Ala Glu Gly Ala Pro Cys
1               5

<210> SEQ ID NO 147
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 147

Cys Lys Asn Glu Ala Gly Ala Pro Cys
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 148

Cys Lys Asn Glu Glu Ala Ala Pro Cys
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 149

Cys Lys Asn Glu Glu Gly Ala Ala Cys
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
```

```
<223> OTHER INFORMATION: May or may not be present

<400> SEQUENCE: 150

Cys Arg Asn Glu Glu Gly Ala Pro Cys
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 151

Cys His Asn Glu Glu Gly Ala Pro Cys
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 152

Cys Lys Asn Glu Asp Gly Ala Pro Cys
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 153

Cys Lys Gln Glu Glu Gly Ala Pro Cys
1               5

<210> SEQ ID NO 154
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 154

Cys Lys Ser Glu Glu Gly Ala Pro Cys
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 155

Cys Lys Asn Asp Asp Gly Ala Pro Cys
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 156

Cys Lys Pro Ser Phe Lys Asn Glu Cys
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 157
```

```
Cys Gln Pro Ser Phe Ala Met Glu Cys
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 158

Cys Ser Pro Ser Phe Lys Gln Glu Cys
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 159

Cys Thr Pro Ser Trp Lys Gly Glu Cys
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 160

Cys Asp Pro Ser Phe Ala Leu Glu Cys
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
```

```
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 161

Cys Leu Pro Ser Phe Arg Leu Glu Cys
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 162

Cys Glu Pro Asn Ser Arg Met Asp Cys
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 163

Cys Gln Pro Ser Ser Lys Leu Asp Cys
1               5

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (14)..(14)
<223> OTHER INFORMATION: May or may not be present

<400> SEQUENCE: 164

Cys His Ile His Gln Ser Lys Phe Phe Asp Ala Pro Pro Cys
1               5                   10
```

```
<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 165

Cys Gln Ala Ser Phe Ala Met Glu Cys
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 166

Cys Thr Ala Ser Trp Lys Gly Glu Cys
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 167

Cys Gln Ala Ser Ser Lys Leu Asp Cys
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
```

```
<222> LOCATION: (9)..(9)
<223> OTHER INFORMATION: May or may not be present

<400> SEQUENCE: 168

Cys Gln Pro Ala Phe Ala Met Glu Cys
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 169

Cys Thr Pro Ala Trp Lys Gly Glu Cys
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 170

Cys Gln Pro Ala Ser Lys Leu Asp Cys
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 171

Cys Gln Pro Ser Phe Ala Met Ala Cys
1               5

<210> SEQ ID NO 172
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 172

Cys Thr Pro Ser Trp Lys Gly Ala Cys
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 173

Cys Gln Pro Ser Ser Lys Leu Ala Cys
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 174

Cys Ala Pro Ser Trp Lys Gly Glu Cys
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 175
```

```
Cys Thr Pro Ser Ala Lys Gly Glu Cys
1               5
```

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 176

```
Cys Thr Pro Ser Trp Ala Gly Glu Cys
1               5
```

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 177

```
Cys Thr Pro Ser Trp Lys Ala Glu Cys
1               5
```

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 178

```
Cys Thr Pro Ser Trp Lys Gly Glu Cys
1               5
```

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:

```
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 179

Cys Arg Asn Asp Glu Gly Ala Pro Cys
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 180

Cys Arg Asn Glu Asp Gly Ala Pro Cys
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 181

Cys Arg Gln Glu Glu Gly Ala Pro Cys
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 182

Cys Arg Ser Glu Glu Gly Ala Pro Cys
1               5
```

```
<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 183

Cys Ala Asn Asp Glu Gly Ala Pro Cys
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 184

Cys Ala Asn Glu Asp Gly Ala Pro Cys
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 185

Cys His Ser Glu Glu Gly Ala Pro Cys
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
```

```
<221> NAME/KEY: misc_feature
<222> LOCATION: (9)..(9)
<223> OTHER INFORMATION: May or may not be present

<400> SEQUENCE: 186

Cys Ala Ser Glu Glu Gly Ala Pro Cys
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 187

Cys His Asn Glu Asp Gly Ala Pro Cys
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 188

Cys His Asn Asp Glu Gly Ala Pro Cys
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 189

Cys Arg Asn Ala Glu Gly Ala Pro Cys
1               5

<210> SEQ ID NO 190
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 190

Cys His Asn Ala Glu Gly Ala Pro Cys
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 191

Cys Lys Ser Ala Glu Gly Ala Pro Cys
1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 192

Cys Lys Ser Asp Glu Gly Ala Pro Cys
1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present
```

```
<400> SEQUENCE: 193

Cys Lys Ser Glu Asp Gly Ala Pro Cys
1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 194

Cys Arg Gln Asp Glu Gly Ala Pro Cys
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 195

Cys Arg Gln Glu Asp Gly Ala Pro Cys
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 196

Cys His Ser Ala Glu Gly Ala Pro Cys
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
```

```
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 197

Cys Arg Ser Ala Glu Gly Ala Pro Cys
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 198

Cys Arg Ser Asp Glu Gly Ala Pro Cys
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 199

Cys Arg Ser Glu Asp Gly Ala Pro Cys
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 200

Cys His Ser Asp Glu Gly Ala Pro Cys
1               5
```

```
<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 201

Cys His Ser Glu Asp Gly Ala Pro Cys
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (9)..(9)
<223> OTHER INFORMATION: May or may not be present

<400> SEQUENCE: 202

Cys Arg Gln Asp Asp Gly Ala Pro Cys
1               5

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      mimotope peptide

<400> SEQUENCE: 203

Leu Gly Lys Asn Glu Glu Gly Ala Pro Gln
1               5                   10

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      mimotope peptide
<220> FEATURE:
<221> NAME/KEY: MOD_RES
<222> LOCATION: (1)..(1)
<223> OTHER INFORMATION: Any amino acid, preferably Cys, and this region
      may or may not be present
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
```

```
<223> OTHER INFORMATION: Asn, Gln, Ser, Gly or Ala
<220> FEATURE:
<221> NAME/KEY: MOD_RES
<222> LOCATION: (4)..(4)
<223> OTHER INFORMATION: Glu, Asp or Ala
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (9)..(9)
<223> OTHER INFORMATION: Any amino acid, preferably Cys, and this region
      may or may not be present
<220> FEATURE:
<223> OTHER INFORMATION: See specification as filed for detailed
      description of substitutions and preferred embodiments

<400> SEQUENCE: 204

Xaa Xaa Xaa Xaa Xaa Gly Ala Pro Xaa
1               5
```